United States Patent [19]
Griffith et al.

[11] Patent Number: 4,841,977
[45] Date of Patent: Jun. 27, 1989

[54] ULTRA-THIN ACOUSTIC TRANSDUCER AND BALLOON CATHETER USING SAME IN IMAGING ARRAY SUBASSEMBLY

[75] Inventors: James M. Griffith, Idaho Falls, Id.; Mario Maciel, Phelan, Calif.; Joseph Pope, Newport Beach, Calif.; Walter L. Henry, South Laguna, Calif.; Paul J. Zalesky, Huntington Beach, Calif.

[73] Assignee: Inter Therapy, Inc., Costa Mesa, Calif.

[21] Appl. No.: 53,692

[22] Filed: May 26, 1987

[51] Int. Cl.$^4$ ............................................... A61B 8/12
[52] U.S. Cl. ........................... 128/660.03; 128/662.05; 29/25.35
[58] Field of Search ...................... 128/344, 348.1, 772, 128/660, 661, 663, 642, 692, 660.03, 660.06; 29/25.35

[56] References Cited

U.S. PATENT DOCUMENTS

| | | | |
|---|---|---|---|
| 3,542,014 | 11/1970 | Peronneau | 128/660 |
| 3,779,234 | 12/1973 | Eggleton et al. | 128/662.06 |
| 3,817,089 | 6/1974 | Eggleton et al. | 128/661 X |
| 3,938,502 | 2/1976 | Bom | 128/660 |
| 4,146,019 | 3/1979 | Bass et al. | 128/6 |
| 4,176,662 | 12/1979 | Fazer | 128/6 |
| 4,319,580 | 3/1982 | Colley et al. | 128/660 |
| 4,327,738 | 5/1982 | Green et al. | 128/660 |
| 4,349,032 | 9/1982 | Koyata | 128/662.06 |
| 4,354,501 | 10/1982 | Colley et al. | 128/662.06 |
| 4,375,818 | 3/1983 | Suwaki et al. | 128/662.06 |
| 4,391,282 | 7/1983 | Ando et al. | 128/662.06 |
| 4,408,612 | 10/1983 | Utsugi | 128/662.06 |
| 4,433,692 | 2/1984 | Baba | 128/662.06 |
| 4,442,842 | 4/1984 | Baba | 128/662.06 |
| 4,446,395 | 5/1984 | Hadjicostis | 310/327 |
| 4,462,408 | 7/1984 | Silverstein et al. | 128/660 |
| 4,466,443 | 8/1984 | Utsugi | 128/662.06 |
| 4,543,960 | 10/1985 | Harui et al. | 128/662.06 |
| 4,567,898 | 2/1986 | Plugge et al. | 128/660 |
| 4,576,177 | 3/1986 | Webster, Jr. | 128/660 |
| 4,589,419 | 5/1986 | Laughlin et al. | 128/663 |
| 4,665,925 | 5/1987 | Millar | 128/660 |
| 4,672,963 | 6/1987 | Barken | 128/660 |

FOREIGN PATENT DOCUMENTS

| | | | |
|---|---|---|---|
| 0088620 | 9/1983 | European Pat. Off. | 128/662.06 |
| 0139574 | 5/1985 | European Pat. Off. | 128/662.06 |
| 0234951 | 9/1987 | European Pat. Off. | 128/662.06 |
| 2758039 | 7/1979 | Fed. Rep. of Germany | 128/663 |
| 2424733 | 11/1979 | France | 128/662.06 |
| 2584288 | 1/1987 | France | 128/663 |

OTHER PUBLICATIONS

Martin, R. W. et al., "An Ultrasonic Catheter for Intravascular Measurement of Blood Flow: Technical Details", Trans. on Sonics & Ultrasonics, vol. Su-27 #6.
Wells, P.N.T. "Biomedical Ultrasonics", Academic Press, N.Y. 1977, p. 20 (copy AU335).
"High Speed Solution of 2nd Order Curves With Special Application to Planar Sections of Blood Vessels", Roy W. Martin, *Computer Programs in Biomedicine*, vol. 13, (1981) pp. 45-60, Elsevier/North-Holland Biomedical Press.
"Applicability of Ultrasonic Tissue Characterization for Longitudinal Assessment and Differentiation of Calcification and Fibrosis in Cardiomyopathy", Julio E. Perez, MD. et al., *Journal of the American College of Cardiology*, vol. 4, No. 1, (Jul. 1984) pp. 88-95.

(List continued on next page.)

*Primary Examiner*—Francis Jaworski
*Attorney, Agent, or Firm*—Nixon & Vanderhye

[57] ABSTRACT

An array of miniature ultrasound crystals mounted on preassembled subassembly which is, in turn, mounted on a small lumen catheter provides dimensional and other quantitative information relating to arterial wall geometry and character at disease or obstruction sites. Balloons also mounted to the catheter make it possible to use the catheter for the angioplasty (PCTA) procedure while actually imaging, in real time, the artery being dilatated and unblocked by the procedure. Efficient, highly miniature transducers are presented along with several different configurations for catheter structures containing fluid lumen, through-lumen, and electrical microcable assemblies for conducting electrical signals to and from the transducers.

33 Claims, 14 Drawing Sheets

OTHER PUBLICATIONS

"In Vitro and In Vivo Studies Using a 4F Pulsed Doppler Velocimeter Catheter System", W. F. Voyles et al., Lovelace Medical Foundation, University of New Mexico School of Medicine and Baylor College of Medicine, ISA (1984) pp. 17–23.

"High Frequency Ultrasound Guidance of Laser Angioplasty", H. J. Geschwind et al., Abstract #1866, *Circulation*, vol. 74, Supp. II, (Oct. 1986).

"Ultrasonic Instrumentation for Cardiovascular Studies", C. J. Hartley et al., Baylor College of Medicine, Grant #2 R01 HL, 22512-09, Devices and Technology *Branch Contractor Meeting*, (Dec. 9–10, 1986), pp. 65.

"Stroke Volume Measurement With An Ultrasonic Catheter Tip System", R. W. Martin et al., *Ultrasound in Medicine*, vol. 3A, (New York, 1977), pp. 23–29.

"Signal Enhancement For Automatic Identification of Arterial Wall Echos From An Intravessel Scanner", R. W. Martin et al., *Ultrasound in Medicine*, vol. 4, (New York, 1978), p. 417–431.

"Anatomical and Pathological Aspects in Ultrasonic Endoscopy For GI Tract", Y. Tanaka et al., *Scandinavian Journal Gastroenterol*, vol. 19, Supp. 94, (1984), pp. 43–50.

"Coronary Atherosclerosis Causes Remodeling of Arterial Geometry: Demonstration by High–Frequency Epicardial Echocardiography", David D. McPherson et al., Abstract #1864, *Circulation*, vol. 74, Supp. II, (Oct. 1986).

"An Ultrasonic Intracardiac Scanner", N. Bom et al., *Ultrasonics*, (Mar. 1972), pp. 72–76.

"Construction of a Circular Ultrasonic Array With Miniature Elements for Cardiac Application", Lancee et al., *Proceedings of the 2nd European Congress On Ultrasonics in Medicine*, Munich Germany (May 1, 1985), pp. 49–53.

"Transluminal Dilatation of Coronary–Artery Stenosis", A. P. Grüntzig, (Letter to the Editor), *The Lancet*, (Feb. 4, 1978), p. 263.

"Coronary Angioplasty: 1986", Reeder et al., *Modern Concepts of Cardiovascular Disease*, vol. 55, No. 10, (Oct. 1986), pp. 49–53.

"Acoustic Properties of Tungsten–Vinyl Composites", Sidney Lees, Robert S. Gilmore, Paul R. Kranz, *IEEE Transactions on Sonics and Ultrasonics*, vol. SU–20, No. 1, (Jan. 1973).

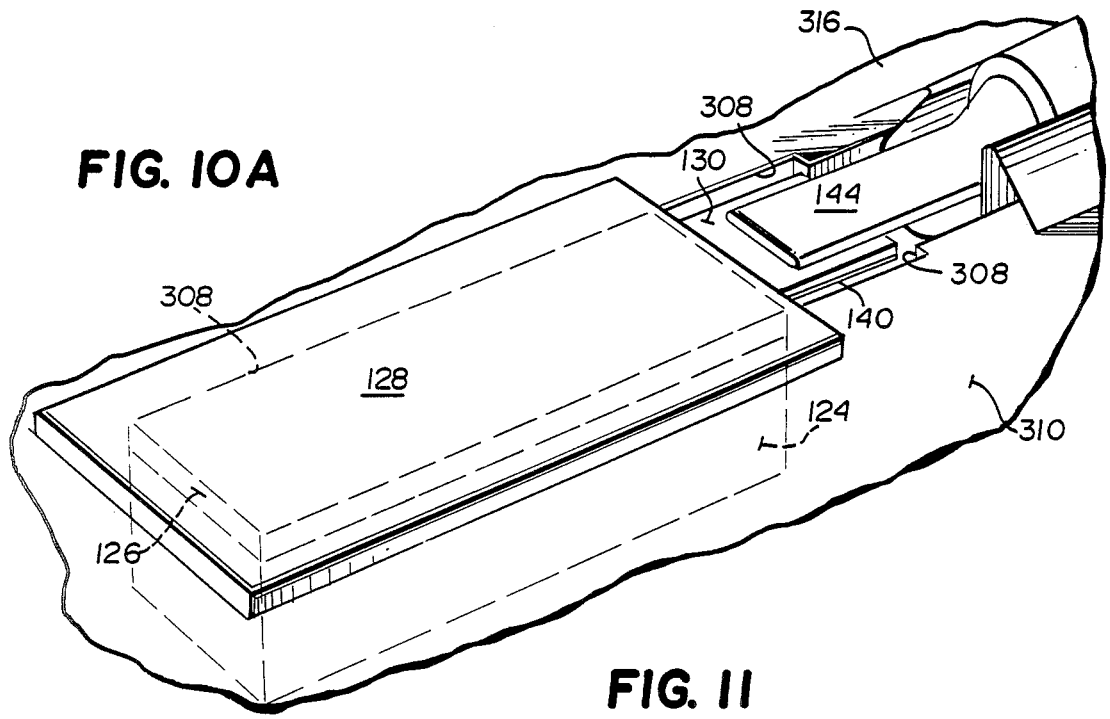
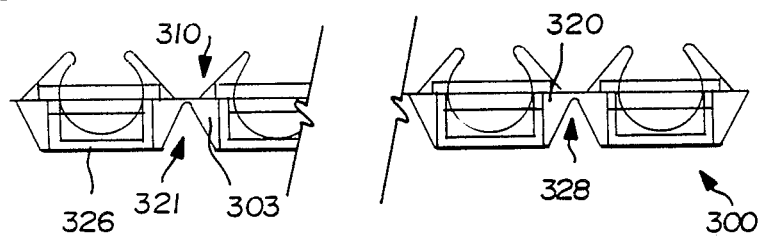
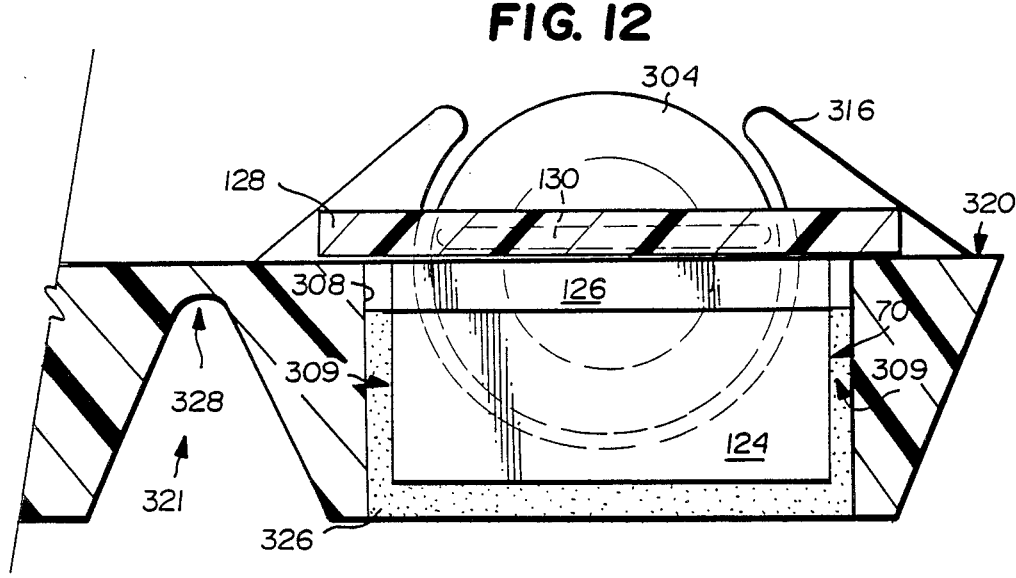

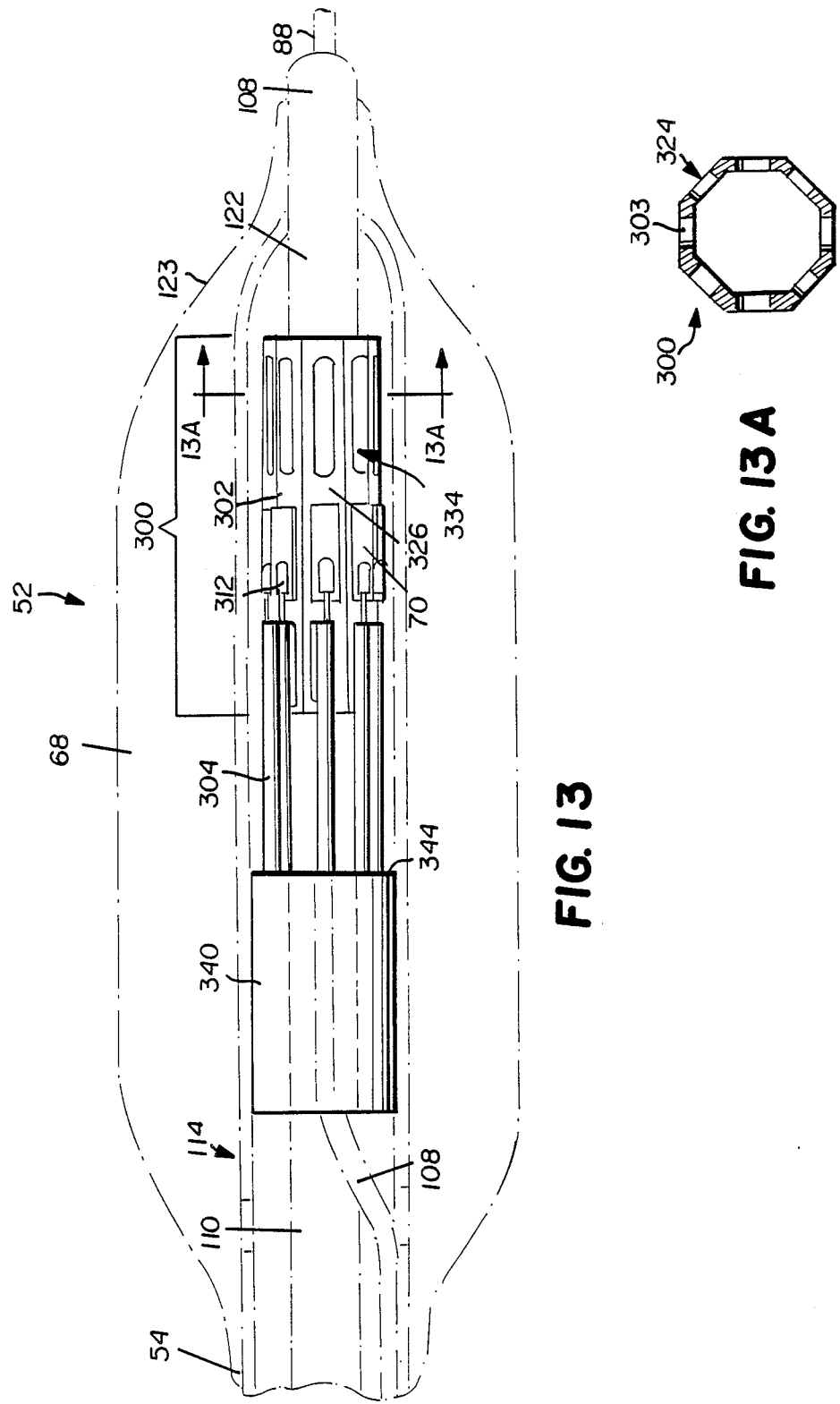

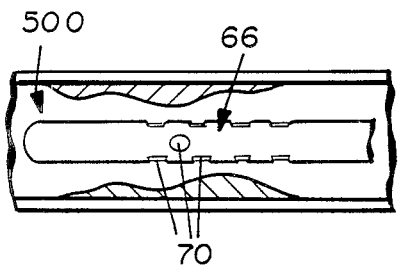
FIG. 24
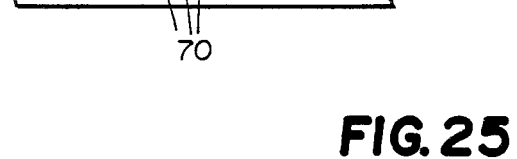
FIG. 25
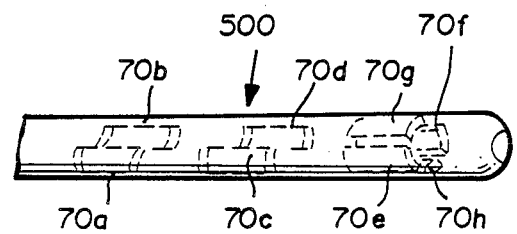
FIG. 26
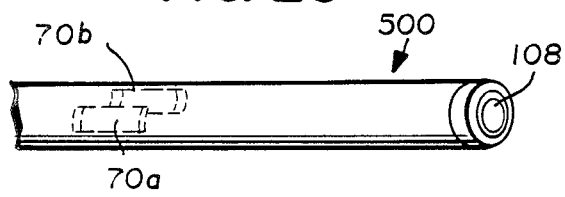
FIG. 27
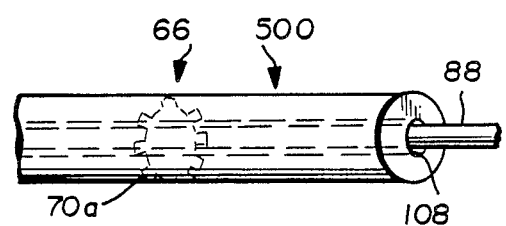
FIG. 28
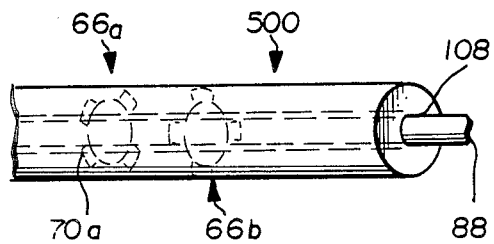
FIG. 29
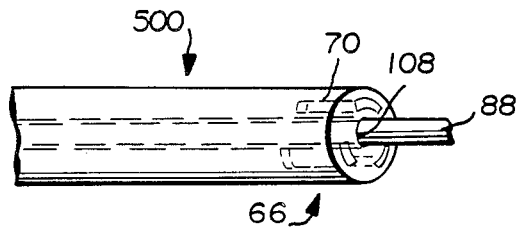

ULTRA-THIN ACOUSTIC TRANSDUCER AND BALLOON CATHETER USING SAME IN IMAGING ARRAY SUBASSEMBLY

This invention generally relates to ultrasound imaging of blood vessel geometry and associated tissue character. More particularly, the present invention relates to an ultra-thin acoustic transducer and to an angioplasty balloon catheter using an array subassembly of same for providing an ultrasound imaging capability (e.g. for guiding the inflation, positioning and end point of the dilatation procedure). The catheter provides a coronary or peripheral angioplasty balloon device incorporating ultrasound technology for real-time intravascular imaging of blood vessels and arteries before, during and after an interventional angioplasty procedure.

Intravascular catheters which include ultrasound imaging crystal arrays have been proposed in the past. It is known to mount a piezoelectric crystal element on or within a catheter of the type which can be inserted into a blood vessel. Once the catheter has been inserted into a blood vessel, the crystal element is electrically excited to cause it to emit ultrasonic energy into the surrounding tissue. While much of the emitted energy is absorbed by the tissue, some of the energy is reflected back toward the crystal element (with reflection occurring principally at interfaces between different types of materials, e.g., the interface between blood and the vascular wall, the interface between blood and lesions adhered to the vascular wall, etc.). The crystal element produces weak electrical signals in response to mechanical excitation by the returning reflected ("echo") ultrasonic energy. These weak electrical signals can be used to determine the geometry and other characteristics of the blood vessel and lesions within the vessel.

Below is a non-exhaustive list of references which are generally relevant in disclosing intravascular catheters (and other) ultrasound imaging systems:

"High Speed Solution of 2nd Order Curves With Special Application to Planar Sections of Blood Vessels", Roy W. Martin, *Computer Programs in Biomedicine,* Vol. 13, (1981), pp. 45-60, Elsevier/North-Holland Biomedical Press.

"Applicability of Ultrasonic Tissue Characterization for Longitudinal Assessment and Differentiation of Calcification and Fibrosis in Cardiomyopathy", Julio E. Perez, MD. et al, *Journal of the American College of Cardiology,* Vol. 4, No. 1, (July 1984), pp. 88-95.

"In Vitro and In Vivo Studies using a 4F Pulsed Doppler Velocimeter Catheter System, W. F. Voyles et al, Lovelace Medical Foundation, University of New Mexico School of Medicine and Baylor College of Medicine, ISA (1984), pp. 17-23.

"High Frequency Ultrasound Guidance of Laser Angioplasty", H. J. Geschwind et al, Abstract #1866, *Circulation,* Vol. 74, Supp II, (Oct. 1986).

"Ultrasonic Instrumentation for Cardiovascular Studies", C. J. Hartley et al; Baylor College of Medicine, Grant #2, RO1 HL 22512-09, Devices and Technology Branch Contractor Meeting, (Dec. 8-10, 1986), pp. 65.

"Stroke Volume Measurement With an Ultrasonic Catheter Ty System", R. W. Martin et al *Ultrasound in Medicine,* Vol. 3, New York, (1977), pp. 23-29.

"Signal Enhancement For Automatic Application of Arterial Wall Echos From Cardiovascular Scanner", R. W. Martin et al, *Ultrasound in Medicine,* Vol. 4, (New York, 1978), p. 431.

Anatomical and Pathological Aspects in Ultrasonic Endoscopy For GI Tract", Y. Panaha et al, *Scandinavian Journal Gastroenterol,* Vol. 19, Supp. 94, (1984), pp. 43-50.

"Coronary Atherosclerosis Causes Remodeling of Arterial Geometry: Demonstration by High-Frequency Epicardial Echocardiography", David D. McPherson et al, Abstract #1864, *Circulation,* Vol 74, Supp. II, (Oct. 1986).

N. Bom et al, *An Ultrasonic Intercardiac Scanner,* Ultrasonico (March 1972), pp. 72-76.

LanCee et al, "Construction of a Circular Ultrasonic Array With Miniature Elements for Cardiac Application", Proceedings of the 2d European Congress on Ultrasonics in Medicine, Munich, Germany (May 1, 1985), pp. 49-53.

U.S. Pat. No. 3,542,014—Peronneau (1970)
U.S. Pat. No. 3,938,502—Bom (1976)
U.S. Pat. No. 4,319,580—Colley et al (1982)
U.S. Pat. No. 4,327,738—Green et al (1982)
U.S. Pat. No. 4,462,408—Silverstein et al (1984)
U.S. Pat. No. 4,576,177—Webster Jr.
U.S. Pat. No. 4,432,692—
U.S. Pat. No. 4,567,898—

The Geschwind et al paper describes a non-invasive (i.e., extra vascular) ultrasound system used to monitor echoes from bubbles caused by tissue vaporization under the influence of laser angioplasty.

Hartley et al describes the use of a focused, unbacked (i.e., air-backed) submillimeter (e.g., 0.5×1.0 millimeter) crystal operating at a frequency of about 20 MHz to produce close-range, high-resolution vascular imaging during the laser angioplasty procedure. This paper teaches mounting the air-backed crystal to the side of a rigid 17-gauge needle, and rotating the needle manually to obtain a 360° image with a resolution approaching 0.2 millimeters.

The Martin article appearing in *Computer Programs in Biomedicine* discloses a computer program which determines blood vessel areas rapidly in response to signals produced by an intravascular ultrasonic catheter.

Perez et al teach generating images of hamster hearts using broadband, focused piezoelectric ultrasound transducers acting as both transmitter and receiver.

Voyles et al discloses a 20 MHz transducer tipped catheter having a circular 1.0 millimeter PZT-5 crystal. The crystal is excited by a pulse repetition frequency of 62.5 KHz to provide blood velocity measurements within an artery.

Colley et al discloses an esophageal catheter having ultrasonic transducers mounted within it for detecting air emboli in the blood of an incorporeal blood vessel.

Perroneaux uses a pair of opposingly disposed ultrasonic transducers on the circumference of a catheter (near to but spaced back from the distal end) for measuring the internal diameter of a cardiovascular cavity.

Bom is directed to a cardiovascular catheter having a circumferential array of at least four equidistantly distributed ultrasonic transducers located near the distal end of the catheter.

Silverstein et al discloses an ultrasonic endoscope having an elongated array of ultrasonic transducers mounted so as to permit the structure to remain flexible.

Ultrasonic cardiovascular catheters developed in the past have some significant drawbacks. The miniaturization of ultrasonic technology for medical intravascular applications raises significant technical problems which have not been solved in the past. For example, the reliability of intravascular ultrasound probes has been relatively poor, and fabrication is so difficult that manufacturing yields are extremely low (significantly raising the cost of such catheters).

Perhaps more importantly, past efforts have failed to produce a practical intravascular interventional catheter. There is much room for further improvement of non-intraventional (diagnostic) ultrasonic catheters. Although ultrasound catheters with no interventional capabilities can be very useful in providing diagnostic information to the physician, it would be still more useful to provide the physician with a real-time image of the portion of the blood vessel being exposed to an interventional procedure such as angioplasty while the procedure is being conducted.

Webster, Jr. '177 discloses an interventional catheter which includes a laser and an ultrasonic transducer. Ultrasound techniques utilizing catheter-mounted ultrasonic transducers locate arteriosclerotic plaque deposits which are then removed by laser irradiation. The value of being able to actually "watch" the section of blood vessel being affected by an international procedure such as laser irradiation of plaque cannot be underestimated.

Intravascular dilatation using a balloon catheter (the so-called "coronary angioplasty" or PTCA procedure) has been found to be extremely effective in treating coronary conditions which were previously treatable only by coronary bypass surgery. See, for example, A. P. Gruentzig, "Transluminal Dilatation of Coronary—Artery Stenosis", (Letter to the Editor) 1 *Lancet*, 263 (1978) for a general discussion of the coronary angioplasty procedure. See also Reeder et al, "Coronary Angioplasty: 1986", 55 *Modern Concepts of Cardiovascular Disease*, No. 10, (Oct. 1986), pp. 49–53, for a discussion of advantages and disadvantages of this procedure.

The conventional angioplasty (PTCA) procedure is becoming more and more popular as an alternative to coronary bypass surgery. Briefly, to perform the PTCA dilatation procedure, the physician inserts a guidewire into the occluded (or otherwise diseased) vessel or artery. A contrast compound (for example, an indicator substance which emits radiation) is usually first injected into the patient's bloodstream so that fluoroscopy can be used to permit the physician to view the occluded vessel. Once the guidewire has reached the occluded section of the vessel or artery, a tubular catheter having a through-lumen is pushed down along the guidewire and guided by the guidewire to the area of blockage. (The "through-lumen" of the catheter is merely an enclosed passage which runs the length of the catheter tube and opens at the catheter distal end—the through-lumen contains and encloses the guidewire.)

Inflatable balloons mounted near the catheter distal end are in fluid communication with another lumen (the "fluid lumen") within the tubular catheter. When fluoroscopy reveals that the catheter distal end has reached the occluded section of the vessel, the physician inflates the catheter balloon (which typically has a well-defined maximum radial dimension so as to avoid possibly undue radial stress on the blood vessel) by pumping pressurized saline solution down through the catheter fluid lumen.

The inflating balloon dilates the blood vessel, causing the elastic vascular wall to expand (actually "cracking" the vessel (to a controlled limited degree) and the lesions or deposits on the vascular wall which form the stenosis)—having the combined effect of internal disruption, plaque fissuring, and stretching of the vessel wall. When the balloon is deflated (by pumping the saline solution back out of the balloon through the fluid lumen), the effective inside cross-sectional diameter of the blood vessel available for blood flow has been significantly increased and that section of vessel is thus unblocked. By repeating the dilatation procedure along the entire length of the blockage, essentially normal (or at least improved) blood flow rate through the blood vessel can be restored.

While fluoroscopy provides limited imaging of the section of the blood vessel undergoing dilatation, the effectiveness of the angioplasty procedure can be significantly increased (and the dangers associated with coronary angioplasty can be significantly decreased) if more detailed real-time images can be made available to the cardiologist. For example, the ability to accurately measure the actual diameter of the vascular wall in real time while it is being dilatated by the inflating catheter balloon would be extremely valuable.

In addition, in a variety of diagnostic and therapeutic settings, the physician requires imaging information regarding local vascular sites in order to determine the nature and extent of disease, therapeutic or medical alternatives, and pre-treatment and/or post-treatment assessments and comparisions. These applications can be satisfied with a catheter having ultrasonic imaging capability but not dilatation capability.

The present invention provides a uniquely designed array of miniature ultrasound crystals mounted on a subassembly carriage which, in turn, is mounted on or within a small lumen catheter to provide quantitative assessment of arterial wall geometry and character at disease or obstruction sites. The present invention can be used in both intra-operative and percutaneous (cardiac catheterization laboratory) applications to provide real-time, quantitative peri-procedure information which represents a quantum leap in sophistication of PTCA (and other intravascular imaging) procedures as compared to currently used pre-procedure and post-procedure angiograms. The current increase in use of PTCA procedures will be further augmented by the ultrasound imaging capabilities of the present invention.

The imaging system of the present invention provides a catheter-mounted, ultrasound-imaging device usable in providing real-time, two-dimensional images in small, curved, blood vessels such as the coronary arteries.

An important feature of the invention is the miniaturization of (and associated fabrication process for) ultrasonic transducers, plus incorporation of the miniature transducers within a subassembly "carriage" having its own structural integrity. For example, prior electro acoustic transducers have typically used a one-half wavelength thick active layer plus a backing layer in excess of 0.25 inch. However, the present invention makes it possible to realize transducers having a total thickness of as little as 0.0075 inch or less (e.g., by using a one-fourth wavelength active layer plus a thin backing layer of slightly higher acoustic inpedance). The use of a subassembly for mounting an array of such ultra thin transducers greatly facilitates manufacturing and testing while also tending to protect the array in operation.

The catheter provided by the invention in one exemplary configuration includes a catheter body, a multi-functioned catheter proximal end, and a miniaturized ultrasonic transducer (or array of such transducers).

A catheter body polymer segment is the major part of a disposable piece that is inserted into the vascular system and advanced into the coronary arteries over a guidewire. The cross-sectional characteristics of this catheter body preferably meet certain confining criteria, including:

- outside diameter of approximately 0.059 inches or less;
- a lumen or other structure that accommodates insulated electric cables for transmission of power to piezoelectric elements and transmission of received signals from same;
- a through-lumen that accommodates an 0.018±0.001 inch guidewire;
- an inflation/deflation ("fluid") lumen for inflatiing and deflating an interventional balloon with a saline/contrast medium;
- a design that accommodates dilatating polymer balloons ranging from 1.5 to 4.5 millimeters in diameter, and 1.0 to 3.0 centimeters in length;
- stiffness or flexibility characteristics that enable the catheter body to be maneuvered through small, tortuous vessels such as the coronary arteries; and
- a surface property that produces a minimum friction so that the catheter body can be advanced through a further, guiding catheter insertion device towards the coronary arteries.

Required functional characteristics of the catheter body can be achieved by providing:

(a) a polymer extrusion in a specific configuration (e.g., defining a "smile" or crescent-shaped internal lumen) which meets the above-mentioned coronary catheter requirements; or (b) an assembly or bundle of small tubules or arrangement of tubules and cables.

A multi-functioned proximal end to the catheter device is provided to permit the device to be interfaced with external equipment. This proximal end is quite complex since it enables connection to outside-the-patient electrical, mechanical, and fluid paths necessary for operation of the catheter. Specifically, the proximal end accommodates low-impedance electrical cable connectors for energization of and reception of signals from the ultrasound transducer array; an integral fluid path for insertion and removal of a steerable guidewire and/or withdrawal of blood samples and/or injection of pharmacological or contrast or other agents; and an integral fluid path for inflation/deflation of the dilating balloon via saline mixed with contrast material.

An important feature of the invention is a miniaturized, functional ultrasound transducer (and an array of such transducers mounted on a separate subassembly) that provides the raw analog acoustic data used to generate a vascular image from acoustic information. The transducer provided by the present invention includes a piezoelectric chip having metallic surfaces (e.g., by vapor depositor or sputtering), a thin backing layer having an acoustic impedance slightly greater than that of the active crystal layer, a faceplate (of one-quarter wavelength) and low impedance electrical leads. Key components of the miniaturized transducer provided by the present invention include:

(a) a piezoelectric ceramic chip with dimensions approximating 0.010 inch (0.256 mm) wide×0.120 inch (5.385 mm) long×0.002 inch (0.51 mm) deep. Porosity of this material must be carefully controlled to avoid short-circuit phenomena from sides of the composition material when electrically contacted (not an issue with larger transducers) while ensuring mechanical integrity and piezoelectric performance criteria. Acceptable candidate composition materials include PZT-5, lead metaniobate, and lead magnesium niobate. Multiple step(s) fabrication processing is required to attain the small dimension needed. The crystal wafer is only one-fourth wavelength thick (as opposed to the typical one-half wavelength). This cuts the electrical impedance in half while increasing the capacitance (a high dielectric constant is also preferred to increase the capacitance electrical inpedance). Typical acoustic impedance of this active layer is on the order of $28 \times 10$ Kg/($M^2$ sec). While PVF films might be thought useable suitable experience has revealed that the lateral dimension of PVF film (e.g., required to obtain sufficiently low electrical impedance) becomes excessive.)

(b) Sputtered conductive metal on either side of the piezoelectric crystal to enable electrical lead attachment (unless the face plate and/or backing layer are themselves conductive). Gold is used in the preferred embodiment to insure mechanical weld integrity, minimal electrical impedance, and processing control. A sputtering process deposits approximately 1,000 to 4,000 angstroms of material on either surface of the crystal. The sputtered surface allows formation of a very low resistance connection comprising a pair of weld junctions with connecting wires (e.g., less than 2–8 ohms).

(c) a backing ledger of a material selected so as to maximize acoustic signals entering into the transducer backing—while minimizing any coherent acoustic reflections therefrom back into the transducer, and causing loss of range resolution. The backing may comprise an epoxy mixed with a powdered dense metal pressure cured directly onto the active ceramic (sputtered) surface. The maximum backing thickness is on the order of 0.020 inch (0.513 mm). One backing composition is formed by mixing 11 grams of 5 micron Tungsten powder (4–8 micron range) with 1.25 grams of a soft rubbery epoxy (1 gram 50A component and 0.25 gram 50B component of Insul Gel epoxy). Another possible backing composition is, by volume, 70% 5 micron Tungsten powder, 21% 0.2 micron Tungsten powder and 9% epoxy applied to the crystal under great pressure (e.g., 12 tons) during the curing of the epoxy component. In general, the backing composition should be chosen to have a slightly greater acoustic impedance (e.g., $30 \times 10^6$ Kg/($M^2$ sec)) than the active transducer layer (e.g., $28 \times 10^6$ Kg/($m^2$ sec)). This insures proper acoustic phasing for the quarter wavelength active layer while also insuring easy passage of acoustic energy into the backing layer. The composition of the cured epoxy and embedded scattering particles helps insure against coherent acoustic reflections back into the active layer.

(d) Flattened electrical lead attachment via spot welding. Gold sputtered copper leads and ceramic elements are used so that the leads may be welded to the ceramic without producing a high resistance connection. Total connection resistance per transducer is preferably held below 5 ohms.

(e) Attachment of a quarter wavelength faceplate material to the active side of the ceramic crystal to ensure maximum transmission of acoustic energy between the piezoelectric crystal and catheter-/blood/tissue interfaces. The faceplating material may be aluminum oxide powder epoxy, with a thickness that is an odd multiple of a quarter wave length. One possible faceplate composition is, by weight, 2 parts $Al_2O_3$ powder and 1 part epoxy (a 50—50 mix of 303 Very Low Viscosity epoxy components available from Mereco Products, Inc.) Faceplate material preferably is attached to a transducer precision cut faceplate directly via a masked or silk-screen printing process (using the adhesive epoxy component of the faceplate composition itself).

The direct attachment of the backing and faceplate layers via the epoxy component of these compositions substantially minimizes any discrete bonding layer (which may cause spurious acoustic responses).

The present invention also provides an array of such miniature ultrasound transducers mounted on a subassembly. An exemplary integral subassembly with its own structural integrity includes an array of eight discrete ultrasound transducers that provide a cross-sectional imaging capability. This exemplary subassembly incorporates the following key features:

an internal structure for polymer bonding to central catheter the body underneath the dilation balloon;
a concentric through-lumen to accommodate at least the portion of the catheter which an 0.018±0.001 inch guidewire (or other size as desired);
an integral, octagonal sleeve of a substantial material (e.g., stainless steel, a solidified polymer, etc.) that serves as a common backing/support structure for all eight transducer elements while providing structural integrity for the subassembly;
a layout of transducer array components that facilitates automated micro-positioner assembly which is useful for accuracy and precision at these very small dimensions.

A distal catheter section is provided which accommodates the ultrasound array subassembly, plus the following:
inflation/deflation lumen and through-lumen;
dilatation balloon attachment;
attachment of ultrasound array subassembly; and
attachment of cabling to subassembly.

The connecting cable may be a parallel-wire transmission line with a controlled wire-spacing to wire-diameter ratio (e.g., of approximately 10:1 to provide approximately 75 ohm impedance for matching to a 75 ohm transducer). If necessary, a small external inductor can be used to "tune out" undesirable capacitive reactance resulting from piezoelectric element capacitance.

Driving and receiving electronics can be similar to those commonly found in medical diagnostic equipment or NDE equipment. The higher operating frequency (approximately equal to 20 MHz) of the present invention is different than that used by conventional pulse-echo equipment, and is highly advantageous since it provides excellent near-field resolution and a range limiting effect.

Images are constructed by conventional techniques developed for PPI radar systems. The images are produced by a "mapping" operation rather than the inherently two-dimensional approach used in optical cameras.

In applications where dilatation is not needed, the catheter cross-section, ultrasound transducer array, and other system components remain as described and the dilatating balloon structure is absent (not required for this application). Exemplary external configurations for these embodiments may be as follows:

(1) A longitudinal array of transducers to produce a longitudinal sectional image of the vascular segment;
(2) A circular, radial array of transducers to produce a radial (cross-sectional) image at a particular vascular site;
(3) A staggered, circular, radial array of transducers to produce a radial (cross-sectional) image at a particular vascular site;
(4) A circular array of transducers located at the catheter distal end, or recessed 0–2 cm from the distal end of the catheter or probe, with an energized surface facing in a "look-ahead" position to produce an axial image in a vascular section. Individual transducer elements may be angulated from 0 to 45 degrees from the vascular axis if desired to produce different angle images. If recessed from the tip, polyethylene or similar polymer material is interposed between the transducer and the tip end to provide sufficient transmissivity of ultrasound energy for image generation.

The catheter of the present invention can be used to provide extremely valuable real-time measurements of internal blood vessel lumen diameter and external vessel diameter, as well as characterization of tissue cross-section and blood flow surface, and visualization of arterial motion in response to intervention.

The present invention significantly enhances the physician's capability for controlling and monitoring a vascular or related procedure, as the real-time image information (which can be displayed on the face of an oscilloscope or equivalent device) provides previously unavailable data regarding the geometry and tissue character of diseased vascular segments. The associated ability to record such patient-specific information further enhances the physician's ability to diagnose and prognose vascular or related disease.

BRIEF DESCRIPTION OF THE DRAWINGS

These and other features and advantages of the present invention will be better and more completely understood by referring to the following detailed description of preferred embodiments in conjunction with the appended sheets of drawings, of which:

FIG. 10A is a detailed view of the assembled array subassembly;

FIG. 11 is an end or section view of the subassembly shown in FIG. 10;

FIG. 12 is a detailed elevated end view of a transducer as installed in the FIG. 10 subassembly;

FIG. 13 is an elevated perspective view of the fabricated transducer array subassembly as shown in FIG. 10 wrapped around a through-lumen and bonded within a balloon catheter body;

FIG. 13A is an elevated view in cross-section of the FIG. 13 subassembly;

FIG. 24 is an elevated perspective view of a non-interventional, diagnostic ultrasound probe of the present invention within a blood vessel;

FIGS. 25–29 are elevated perspective views of various alternate configurations for the FIG. 24 diagnostic probe;

DETAILED DESCRIPTION OF PREFERRED EMBODIMENTS

Figure 1:
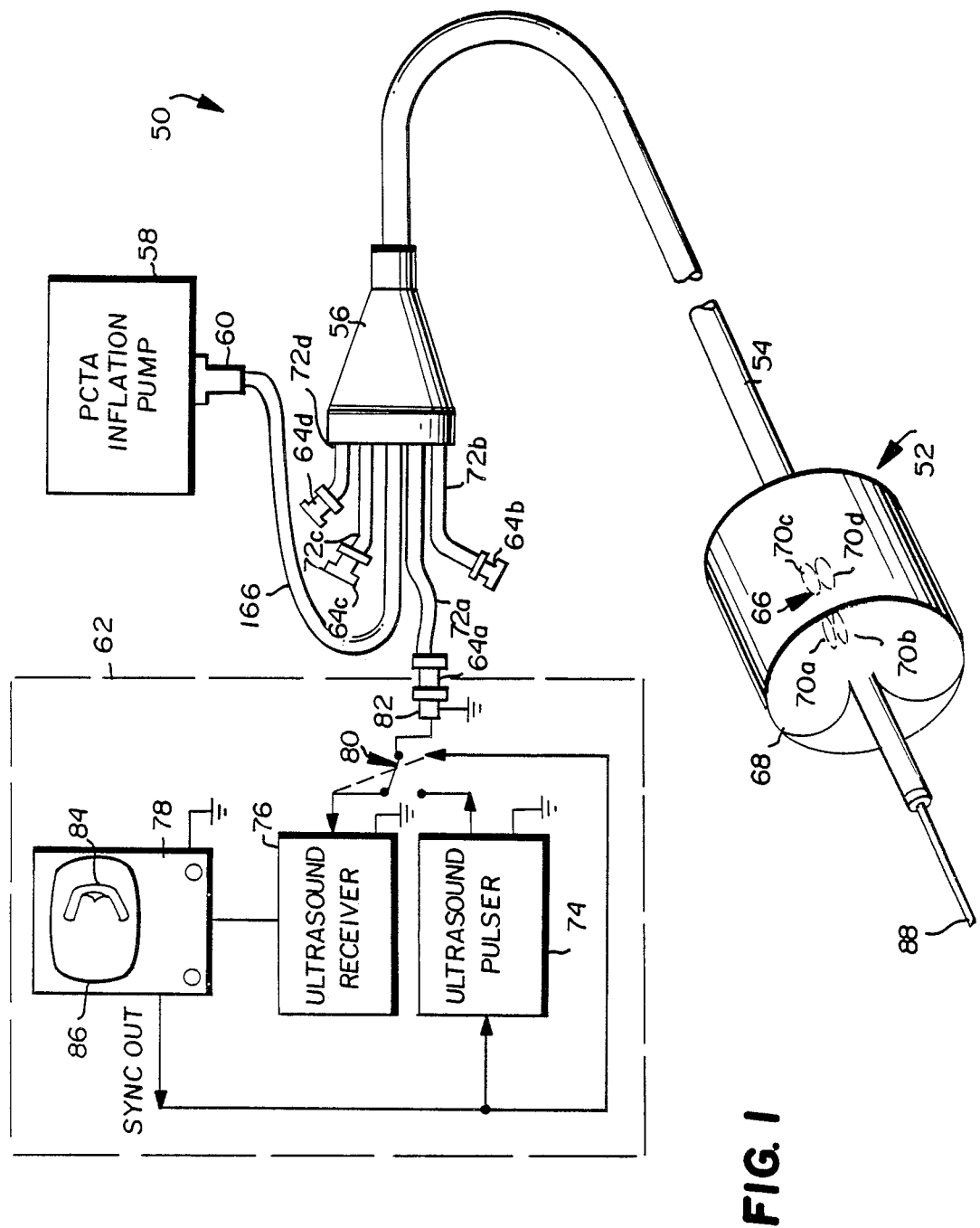
FIG. 1 is a schematic diagram of a presently preferred exemplary embodiment of an angioplasty (PCTA) system of the present invention including an ultrasound balloon (dilatation) catheter.

FIG. 1 is a schematic diagram of the presently preferred exemplary embodiment of an angioplasty/imaging system 50 of the present invention.

System 50 includes a catheter 52 connected by a catheter tube 54 to a proximal connector 56. Proximal connector 56 connects catheter tube 54 to a conventional PCTA inflation pump 58 (via a proximal mechanical connector 60), and also to an ultrasound excitation/imaging device 62 (via conventional miniature coaxial cable connectors 64a–64d).

An ultrasonic transducer array 66 is disposed within and/or about catheter tube 54 and is enveloped by conventional catheter dilatation balloon(s) 68. In the preferred embodiment, array 66 includes several (e.g., four to eight) transducers 70a–70d arranged in opposing pairs. Electrical microcables (not shown) run the length of tube 54 and connect transducer array 66 to proximal connector 56. Connector 56 in turn connects the microcables to miniature coaxial cables 72a–72d (one for each transducer 70) each of which is terminated by a conventional miniature coaxial connector 64.

Ultrasound imaging device 62 of the preferred embodiment includes an ultrasound pulser 74 (e.g., of the type which shock excites a connected electroacoustic transducer by discharging a capacitor thereinto which is precharged to, for example, 100 volts), an ultrasound receiver 76, an oscilloscope 78, and an electronic switch 80. Ultrasound pulser 74 produces a pulse signal (of a desired magnitude and shape which is applied to excite one or more of transducers 70 (via a coaxial connector 82 mating with a corresponding one of transducer connectors 64a–64b). Electronic switch 80 connects mating coaxial connector 82 to ultrasound pulser 74 while the pulser produces the pulse, and then connects the coaxial connector to the input of ultrasound receiver 76. Ultrasound receiver 76 performs conventional signal processing operations on electrical signals generated by mechanical excitation of transducers 70a–70d (e.g., amplification, noise reduction and the like) and applies the processed signals to the input of oscilloscope 78. Scope 78 generates an ultrasound image 84 on CRT 86 (or other equivalent display device) of the vascular structures reflecting ultrasonic energy toward array 66 using conventional PPI (radar) algorithms. As will be appreciated, switch 80 can be conventionally arranged so as to multiplex connections between all of the transducer cable connections 64a–64d and the ultrasound signal processing circuits 74, 76.

Catheter tube 54 encloses at least two "lumens" (passages) in the preferred embodiment. One of the lumens, called a "through-lumen", contains a guidewire 88. The other lumen (the "fluid lumen") is used to communicate fluid to and from balloon 68. The fluid lumen is connected via fluid connector 60 to inflation pump 58. Inflation pump 58 controls very accurately the amount and pressure of saline solution applied to the fluid lumen within catheter tube 54—and thus controls the degree to which balloon 68 is inflated.

Figure 2:
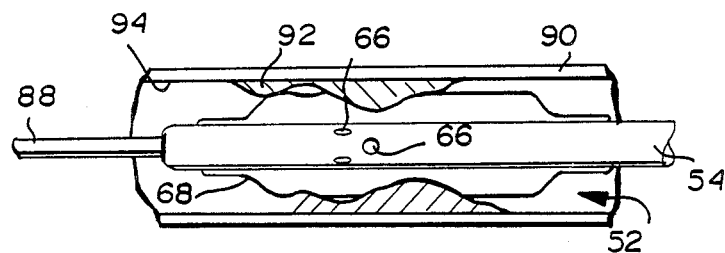
FIG. 2 is an elevated side view of the balloon catheter shown in FIG. 1 after inflation of the balloon.

To use system 50, a cardiologist first inserts guidewire 88 into the blood vessel (e.g., artery) to be imaged and/or dilatated. Once the guidewire is in position, the cardiologist inserts catheter 52 into the artery and pushes it along the guidewire through the artery to a section of the artery of interest. FIG. 2 is a cross-sectional view of catheter 52 positioned within an artery 90 having a lesion 92 on its inner wall 94.

As catheter 52 passes through artery 90 along guidewire 88, the cardiologist can view a cross-sectional image of the artery on display 86 to determine geometry and other characteristics of the artery and also the presence of and geometry of deposits (e.g., plaque) on the inner artery wall 94. Images produced by ultrasound imaging device 62 can be used either alone or in conjunction with other imaging techniques (e.g., fluoroscopy of contrast material injected into the artery via the through-lumen and/or injected into the balloon via the fluid lumen) to locate catheter 52 within the patient's cardiovascular system.

Once catheter 52 is positioned in a partially occluded section of artery 90, the cardiologist can determine the geometry and composition of lesion 92 from images produced by device 62. Based on the detailed and nearly complete dimensional and qualitative description of the arterial wall (and lesions thereon) provided by imaging device 62, the cardiologist can decide whether the interventional angioplasty procedure should be performed on the particular segment of the artery the catheter 52 is disposed within.

If the cardiologist decides to apply dilatation to the segment of artery 90 within which catheter 52 is disposed, he or she actuates inflation pump 58 and applies a stream of fluid to catheter balloon 68 via the fluid lumen. Balloon 68 inflates in response to this fluid stream—thereby expanding the arterial wall 90 and creating fissures in lesion 92. During this process, the cardiologist can view a real-time image of the wall and the lesion generated by imaging device 62, and thus determine (actually measure) the degree to which the wall has been dilatated. Such extremely accurate measurements of the specific section of artery being treated can help to reduce dangers (e.g., over-dilatation) associated with the procedure as well as increase the effectiveness of the procedure (for example, under-dilatation, which has been isolated as a possible cause for restenosis of the dilatated lesion, can be avoided).

Figure 3:
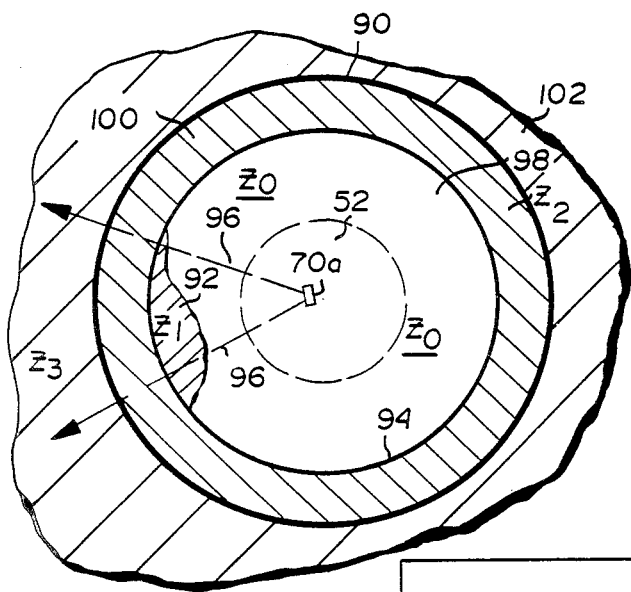
FIG. 3 is a cross-sectional elevated side and schematic view of the vessel shown in FIG. 2.

Ultrasonic pulser 74 produces a short pulse excitation which causes the transducer to "ring" at a predetermined characteristic frequency (about 20 MHz in the preferred embodiment). In this embodiment, ultrasonic transducers 70 have a configuration (which will be explained in greater detail shortly) which cause them to each emit acoustical (ultrasonic) energy at such predetermined frequency in a relatively narrow beam (e.g., along a radially-outwardly extending radiation pattern contained within dotted lines 96 of FIG. 3).

The ultrasonic energy emitted by transducer 70a is absorbed to different degrees by the structures it passes through, depending upon the density and other characteristics of those structures—the energy being absorbed and/or reflected to different degrees by: (a) blood within the artery; (b) lesions on the arterial wall; (c) the arterial wall itself; and (d) tissues surrounding the artery.

Some of the ultrasonic energy emitted by transducers 70 is absorbed by blood 98 passing through artery 90 (assume that blood 98 has an absorption factor of $Z_0$). Some of the ultrasonic energy not absorbed by blood 98 is reflected at the interface between the blood and lesion 92 (and at the interface between the blood and vascular wall 100) back toward ultrasonic transducer 70a. The remainder of the ultrasonic energy emitted by the transducer which is not absorbed by the blood passes into lesion 92 or into vascular wall 100.

Lesion 92 is typically more dense than blood 98, and therefore has a different absorption factor than that of the blood (assume the lesion has an absorption factor of $Z_1$). Much of the ultrasonic energy which passes into lesion 92 is absorbed by the material comprising the lesion. However, some of this ultrasonic energy is reflected back toward ultrasonic transducer 70a at the interface between lesion 92 and inner vascular wall 94, and some of the ultrasonic energy passes into vascular wall 100.

Vascular wall 100 has a different acoustic impedance than that of lesion 92 and blood 98, and therefore absorbs ultrasonic energy to a different degree (assume for the purposes of this example that the vascular wall has an absorption factor of $Z_2$). Some of the ultrasonic energy passing into vascular wall 100 which is not absorbed by the vascular wall is reflected (at the interface between the vascular wall and surrounding tissue 102) back toward ultrasonic transducer 70a. The remaining ultrasonic energy not absorbed by vascular wall 100 passes into the surrounding tissue 102.

Unlike most or all intravascular imaging systems in the prior art, the present invention preferably uses relatively high ultrasonic frequencies (e.g., about 20 MHz). Most of the 20 MHz ultrasonic energy passing into surrounding tissue 102 is absorbed by the tissue. Relatively high ultrasonic frequencies are used in the preferred embodiment in order to maximize absorption of ultrasonic energy by tissue 102 (and minimize reflections from tissue 102 back toward transducers 70)—ultrasonic energy of higher frequencies being absorbed more readily than ultrasonic energy of lower frequencies. An ultrasonic excitation frequency of approximately 20 MHz with a bandwidth of approximately 10 MHz has been found to be satisfactory for this purpose. Because this relatively high excitation frequency is used, the imaging range of transducer 70 is confined to approximately the interface between arterial outer wall 90 and surrounding tissue 102 (1.0 cm distance from the transducer)—exactly the area of interest to the cardiologist. The 20 MHz frequency thus enhances near field resolution and limits effective range.

Electronic switch 80 and ultrasound pulser 74 are synchronized (e.g., using the "synchronization out" signal produced by oscilloscope 78) such that switch 80 connects ultrasonic transducer 70a to ultrasound pulser 74 during the time the pulser is producing a pulse, and electrically connects the ultrasonic transducer to the input of ultrasound receiver 76 during all other times. After ultrasonic pulser 74 produces a pulse to excite ultrasonic transducer 70a, the transducer is disconnected from the pulser and is connected to the input of receiver 76.

Ultrasonic "echo" energy reflected by the interfaces between blood 98, lesion 92, vascular wall 100 and surrounding tissue 102 back toward ultrasonic transducer 70a mechanically excite the transducer, causing it to produce electrical signals responsive to the amplitudes and relative timing of reflected acoustical "echo" signals which reach the transducer. The electrical signals generated by transducers 70 in response to these "echo" signals are amplified by receiver 76 and applied to the input of oscilloscope 78. Scope 78 produces, for example, the image shown in FIG. 4 in response to these "echo" signals (using conventional PPI radar imaging algorithms).

Because of the highly directional (narrow beam) radiation pattern of transducers 70, only signals reflected by structures located within a relatively thin cross-sectional "slice" of artery 90 are received by each transducer and contribute to the image generated by oscilloscope 78. Since the exemplary embodiment uses a finite number of discrete transducers, the resulting PPI type image will be somewhat granular (except to the extent that smoothing and/or extrapolation algorithms are used to "fill in" the missing data points.) Image 84 appearing on the screen 86 of scope 78 thus represents a real-time image of vascular structures of interest in the field near transducer 70a.

The coverage of the image generated depends upon the configuration of transducer array 66—and on the configuration of each of transducers 70. The exemplary configuration of array 66 and transducers 70a-70d will be discussed in great detail shortly. Briefly, transducers 70 are designed to be very efficient (i.e., to direct most of the energy they emit in a narrow beam along a desired path,) and also to be insensitive to reflections received from directions other than the directions in which they emit energy (to reduce noise and image ambiguity).

The angular range over which each transducer 70a-70d emits energy depends on the cross-sectional face area of the transducer. It is desirable to cover a full 360 degrees of the near field with transducer array 66 to explicitly provide a complete image of the artery (although conventional algorithms can be used to "fill in" missing image segments through interpolation and/or partial images may provide sufficient information to a viewer). It is, however, difficult to fabricate highly miniaturized transducers which cover large angles (since the angle of radiation is limited by the size of the transducer active surface).

Figure 5A:
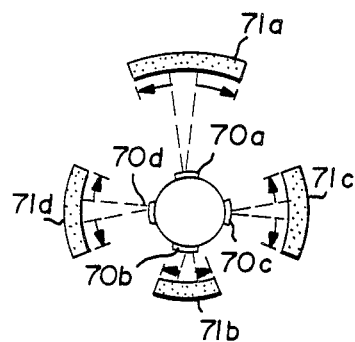
FIGS. 5A–5C are cross-sectional schematic diagrams of simplified images resulting from different crystal array configurations.
Figure 5B:
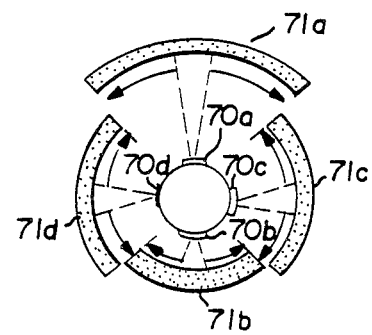
Figure 5C:
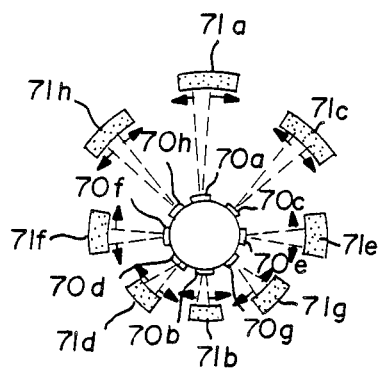

FIGS. 5A-5C show simplified images which may result from three different configurations for transducer array 66. Each transducer 70a-70d-70h in the FIG. 5A-5C arrays is curved to somewhat increase the angular coverage of the transducers.

The FIG. 5A array includes two pairs of opposing transducers 70a-70d each providing image data 71a-71d which is simply accurately expanded so as to effect a 45° degree coverage for a total "coverage" of 50% (45 degree gaps between the "coverage" of adjacent transducers reduce the information within the image).

The FIG. 5B array configuration also includes two pairs of opposing transducers 70a-70d, but these transducers produce data which is accurately expanded so as to provide a pseudo image having 90 degree coverage for each transducer or 100% total "coverage". The FIG. 5B transducers may be larger in size than those shown in FIG. 5A, and therefore may be more difficult to "fit" into a small catheter body.

Figure 5D:
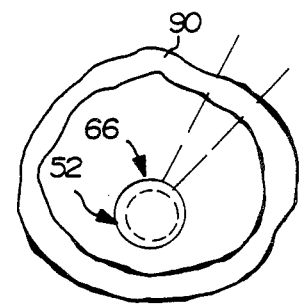
FIG. 5D is a schematic diagram in cross-section of a blood vessel and in-dwelling catheter of the present invention having a radial 8-transducer array configuration.

The array shown in FIG. 5C includes four pairs of opposing transducers 70a-70h (for a total of eight transducers) each producing data 71a-71h which is accurately expanded so as to provide a 22 degree coverage for a total of 50% image coverage. FIG. 5D is a cross-sectional schematic diagram of the FIG. 5C array disposed in a catheter body and also showing (in dotted line) the beam path of an arbitrary one of the eight transducers. While the explicit image provided by the FIG. 5C array covers only 50% of the total area of interest, the granular image is complete enough to permit missing details to easily be filled in mentally by the viewer—since the probability is very high that all significant features of the artery will be at least partially within the coverage of at least one transducer.

Figure 4:
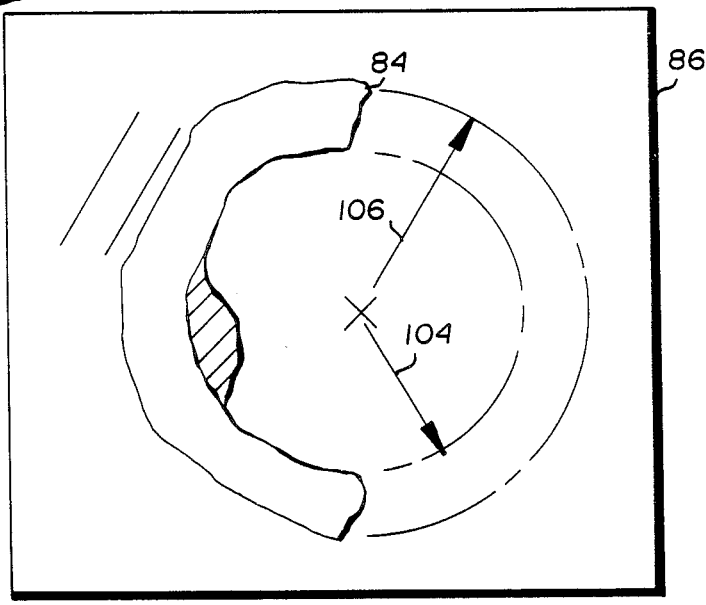
FIG. 4 is an exemplary ultrasound image produced by the system of FIG. 1.

From the typical visualization pattern shown in FIG. 4 produced by system 50, a cardiologist can make a real-time dimensional measurement of the internal lumen diameter of the section of artery 90 which catheter 52 is positioned within (dimension 104 shown in FIG. 4), and can also make a real-time dimensional measurement of the external diameter of artery 90 (dimension 106 shown in FIG. 4). In addition, the cardiologist can characterize the cross-section of tissue and the blood flow surface of the section of artery 90 being images. Based upon these real-time measurements and characterizations, the cardiologist may conclude that dilatation of the artery section is necessary, and control inflation pump 58 to deliver saline solution under pressure through the fluid lumen within catheter tube 54, thereby inflating balloon 68 to a desired degree.

During inflation of balloon 68 (and dilatation of artery 90), oscilloscope 78 displays a real-time visualization of arterial motion and response to intervention. The cardiologist can accurately control the degree and duration of inflation of balloon 68 while watching the real-time image of the section of artery being dilated. Because the cardiologist can actually "watch" the section of artery being dilatated while it is being dilatated, the danger of excessive dilatation is minimized and the cardiologist can also make sure sufficient dilation occurs. In addition, because system 50 produces an image of lesion 92 before, during and after intervention, the cardiologist can decide if additional angioplasty repetitions are necessary and can also ascertain the effectiveness of intervention (and thus, the prognosis of the patient and the need for additional therapy).

Figure 6:
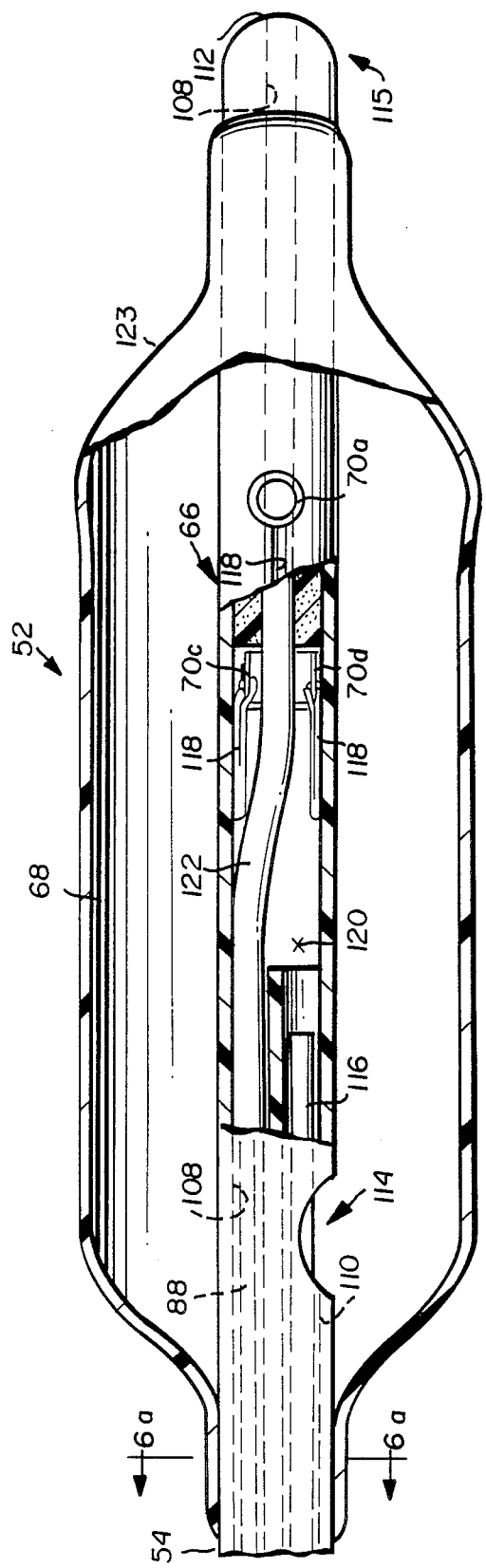
FIG. 6 is a detailed top view in partial cross-section of a first embodiment of the catheter shown in FIG. 1.
Figure 6A:
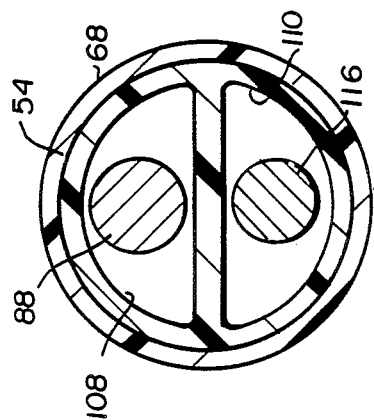
FIG. 6A is an elevated cross-sectional schematic view of the catheter tube of FIG. 6.

FIG. 6 is a top view in partial cross-section of one exemplary embodiment of balloon catheter 52 shown in FIG. 1. Balloon catheter 52 and catheter tube 54 shown in the FIG. 6 embodiment have two different lumens arranged in a "double-D" configuration: A through-lumen 108 (for pressure monitoring and guidewire placement); and a fluid lumen 110 (through which the saline solution flows to inflate balloon 68, see FIG. 6A).

Guidewire 88 is disposed within through-lumen 108 and has a smaller outside diameter than the inside diameter of the through-lumen to allow catheter 52 and catheter tube 54 to "travel" by sliding along the outer surface of the guidewire. Because through-lumen 108 opens into the blood vessel at an opening 112 located at the distal end (tip) 115 of catheter 52, there is a direct fluid connection via the through-lumen between the blood vessel and the proximal end of catheter tube 54. Through-lumen 108 thus can be used for monitoring blood pressure and/or injecting substances (e.g., contrast materials) into the vessel.

An inflation port 114 connects fluid lumen 110 with the interior of balloon 68. Inflation port 114 allows saline solution to flow under pressure from fluid lumen 110 into balloon 68 to inflate the balloon, and also allows saline solution within inflated balloon 68 to flow out of the balloon back into the fluid lumen upon balloon deflation. The cross-sectional area of fluid lumen 110 (and port 114) is sufficiently large to permit rapid deflation of balloon 68—immediately alleviating cardiac dysfunction caused by extended complete occlusion of arteries by inflated balloon 68.

Catheter 52 preferably has an outside diameter of about 0.059 inch (1.513 mm) or less, and accommodates balloons 68 ranging from 1.5 to 4.5 mm in diameter, and 1.0 to 3.0 cm in length. Through-lumen 108 in the preferred embodiment is large enough to accommodate a (e.g., 0.018 inch or 0.462 mm) guidewire. Catheter 52 has conventional stiffness/flexibility characteristics that enable it to be maneuvered through small, tortuous vessels such as the coronary arteries, and an outer surface property that produces minimum friction so that it can be advanced through a guiding cathether as an insertion device toward the coronary arteries.

The body of catheter 52 (FIG. 6) is conventionally fabricated using polymer extrusion, a well-known technology that provides a catheter body with the characteristics described above. In an alternate embodiment, however, the catheter 52 includes an assembly of discrete tubules which are preferably enclosed within a conventional polymer outer tube/shell (as will be explained).

A microcable assembly 116 is located in fluid lumen 110 and runs along the length of catheter 52 and catheter tube 54. Microcable assembly 116 transmits power to transducer array 66, and also transmits received signals from the array (the same cables are used for both outgoing and incoming signals). Microcable assembly 116 contains five insulated electrical leads (one for each of transducers 70a–70d and a sixth acting as a common ground conductor) in one preferred embodiment. Microcable assembly 116 is connected to leads 118 of transducer array 66 at approximately point 120.

In an eight transducer embodiment (FIG. 6B), the number of necessary wires can be reduced to six by using two different common ground lines 600 (each in common with four transducers) and four active lines 602 (each serving two transducers). This reduction in lines is possible because not all of the transducers are active at any given time. (Indeed, in the exemplary embodiments, only one transducer is active at any given time.)

The transducers 70 in array 66 are arranged in two opposing pairs in the embodiment of FIG. 5A. Transducers 70c and 70d are each bonded to through-lumen outer wall 122 and they are offset from one another by 180 degrees. Transducers 70a, 70b are similarly bonded to through-lumen outer wall 122 and are offset from one another by 180 degrees. All of the transducers in array 66 are disposed within the portion of catheter tube 54 enclosed by balloon 68. In general, it is desirable to locate array 66 close to the distal end 123 of balloon 68. However, it would probably be undesirable to position array 66 at distal end 115 of catheter 52, since array 66 in the preferred embodiment is highly directional and might not be capable of imaging the section of artery being dilatated by inflated balloon 68 unless the array is located somewhere directly within that section.

Transducers 70a, 70b are spaced away from transducers 70c, 70d in the preferred embodiment by 90 degrees in rotation and by a short axial distance along catheter tube 54. This preferred configuration allows each of transducers 70a–70d to be operated independently without interfering with the other three transducers in the array.

Figure 7:
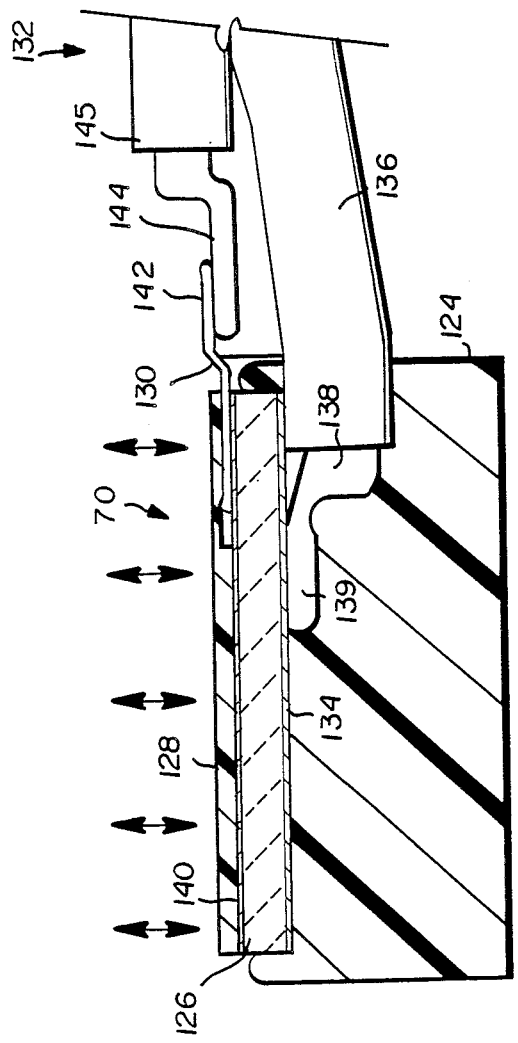
FIG. 7 is an elevated side view of one of the ultrasound transducers shown in FIG. 6.

FIG. 7 is a detailed side view of one of transducers 70 shown in FIG. 6. Transducer 70 includes a backing 124, a ceramic transducer chip 126, a quarter wavelength matching layer 128, and a ribbon connector 130.

Transducer chip 126 is a flat, thin rectangular structure made of piezoelectric material in the preferred embodiment, and is precision cut to resonate at a desired frequency. As is well known, such piezoelectric material mechanically vibrates when excited by an electrical voltage pulse—and produces electric voltage when it is mechanically excited. In the preferred embodiment, chip 126 has dimensions of approximately 0.010 inch wide by 0.120 inch long by almost 0.002 inch thick. It is shock excited by discharging a 100 volt charged capacitor (time constant of about 0.02 microsecond). The area of the transducer is selected so as to provide the requisite acoustic power (watts/cm$^2$) output so as to permit a receiver with a given gain factor to detect the returned echo from artery wall interfaces. Chip 126 should be made from a material with controlled porosity so as to avoid short-circuit phenomena when sides of the chip are electrically contacted while insuring mechanical integrity and meeting piezoelectric performance criteria (i.e., efficient conversion between electrical and mechanical energy). In the preferred embodiment, chip 126 is made from one of the following materials: PZT-5, Lead Metaniobate, and Lead Magnesium Niobate.

Conductive metal is sputtered on upper chip surface 140 and lower chip surface 134 in the preferred embodiment to enable attachment of electrical leads (a bifilar cable including leads 132 and 136 is shown). Gold sputtering is preferably used in order to ensure good mechanical weld integrity, minimize the electrical impedance of the connection, and allow better processing control during fabrication. Conventional sputtering techniques are used to deposit approximately 1,000–4,000 angstroms (or more if required for good conductivity) of gold on surfaces 134 and 140.

A backing 124 is bonded directly to transducer chip lower surface 134 (e.g., via an epoxy component of the backing itself which is cured in place) in order to absorb ultrasonic energy emitted by the transducer chip in a direction toward the bottom of FIG. 7, making transducer element 70 unidirectional (the chip emits very little energy in the direction normal to the plane of FIG. 7). The backing material should have an acoustic impedance (p.c) (e.g., 30 to $40 \times 10^7$ Kg/(M$^2$ sec)). Typically a powdered dense material (e.g., Tungsten) may be incorporated in the backing to increase its acoustic impedance (density times speed of sound in the medium) and to cause scattering of acoustic energy. This also provides the requisite phasing to support use of a thin quarter wavelength thick active transducer 126. If a very very high acoustic impedance material (e.g., platinum, gold or titanium) is used then a thin approximately 0.002 inches thick ($\frac{1}{4}$ wavelength at the excitation frequency of 20 MHz) strip of pure metal may possibly be used as a backing.

Acoustic energy cannot easily penetrate backing 124 to reach transducer chip surface 134—this energy would cause reverberation within the transducer chip and results in a loss of range resolution.

Preferably, backing 124 can be composed of a matrix of tungsten particles suspended in an epoxy or vinyl base which is directly adhered to transducer chip lower surface 134 using the matrix carrier material itself. The diameter of the suspended tungsten particles should be no more than about 10 microns, and the mixture density should be selected so that the acoustic impedance of backing 126 is only slightly higher than that of chip 126.

One flattened bifilar cable lead terminal 139 is welded to transducer lower surface 134 before backing 124 is applied to the transducer chip. (Alternatively, if backing 124 is sufficiently conductive, lead 139 may be connected to its back side instead.) Lead 136 is made of copper and sputtered with gold in the preferred embodiment to decrease connection resistance (the connection resistance is preferably less than 5 ohms). The conductor 138 within lead 136 is flattened at terminal portion 139 where the lead is connected to transducer chip 126 to provide increased conductive surface area, and is welded to the transducer chip with a parallel gap welder.

Conductive ribbon 130 (a flat, thin piece of conductive material which is also gold sputtered or made entirely of gold) is welded to transducer chip upper surface 140 using a parallel gap welder. Ribbon 130 has an extended portion 142 which extends away from the transducer chip in a direction approximately parallel to transducer chip upper surface 140. A flattened terminal portion 144 of bifilar lead 145 is welded to ribbon extended portion 142. Electrical signals applied between leads 132 and 136 cause transducer chip 126 to mechanically vibrate at a predetermined resonant frequency (the piezoelectric effect) in a conventional manner.

Transducer chip 126 has a matching layer 128 provided on the faceplate surface to optimize acoustic matching between the transducer chip and blood/saline. Matching layer 128 in the preferred embodiment is one-quarter wave length thick and has an acoustic impedance which approximates the geometric mean between that of the active chip 126 and the blood/saline material.

This matching layer 128 is provided in the preferred embodiment to ensure maximum transmission of acoustical energy between transducer chip 126 and catheter/blood/tissue interfaces. In the preferred embodiment, matching layer 128 is made of aluminum oxide/epoxy material, and has a thickness which is an odd multiple of a quarter wavelength of the matching layer material (for any given frequency of acoustical energy, wavelength is a function of the propagation velocity of the material the acoustical energy is passing though). Matching layer 128 is directly bonded to the chip surface 140, (e.g., via an adhesive epoxy component of the faceplate material) by masking deposition or "silk screen" printing processes.

Matching layer 128 allows for more efficient transfer of energy between transducer chip 126 and its surrounding media, thus increasing the sensitivity and efficiency of transducer 70.

The electrical input impedance of transducer 70 is important because it is easy to measure and serves as an indicator of other important characteristics. In addition, electrical impedance has direct importance. It must be computed and measured so that cable, transmitter, and receiver impedances can be matched for efficient energy transfer.

Model results have been calculated which are initially useful for component selection, design optimization, and choice of fabrication techniques and materials. The model also assists in setting realistic performance and quality control expectations.

Calculations are based on Mason's equivalent circuit (see, for example, Edmond's book "Methods of Experimental Physics").

Several numerical values were assumed to define the components of transducer 70 and microcable assembly 116. The values were taken from various tables and data sheets. The zero-attenuation assumption for the transducer faceplate depicts an actual faceplate (and matching layer 126) configuration and composition and therefore should be checked for the specific faceplate used.

TABLE I

| Transducer Parameter Values | |
|---|---|
| Parameter | Assumed Value |
| cross-sectional area | $5 \times 10^{-7}$ m$^2$ |
| Z backing | $30 \times 10^6$ kg/(m$^2$ sec) |
| ceramic (EDO PMN #EC-98) | |
| Zo | $27 \times 10^6$ kg/(m$^2$ sec) |
| velocity of sound | 3470 m/sec |
| attenuation | 0.0 nepers/m |
| dielectric | 5500 |
| elastic stiff | $0.94 \times 10^{11}$ N/m$^2$ |
| g, press const | $1.5 \times 10^{-2}$ (V/m)/(N/m$^2$) |
| thickness | $4.3 \times 10^{-5}$ m ($\frac{1}{4}$ wave-length) |
| faceplate (EBL #105) | |
| Zo | $5.5 \times 10^6$ kg/(m$^2$ sec) |
| velocity of sound | 3020 m/sec |
| attenuation | 0.0 nepers/m |
| thickness | $3.8 \times 10^{-5}$ m ($\frac{1}{4}$ wave-length) |

The analysis assumes perfect bonding between the backing 124 and ceramic chip 126, and between the chip and faceplate 128. Clearly, these assumptions are somewhat in error. The model can be corrected to include the effects of bond thickness if additional accuracy is desired.

Results herein ignore cable effects and tuning inductor effects. These effects can be added to the model if additional accuracy is required.

A Tektronix model 2236 ohmmeter has been used to measure the resistance at the welded lead-to-transducer junction. After accounting for the resistance in the ohmmeter connections, the weld joints should measure one or two ohms. This value is substantially below the ceramic and cable impedances and can therefore be ignored.

Figure 8A:
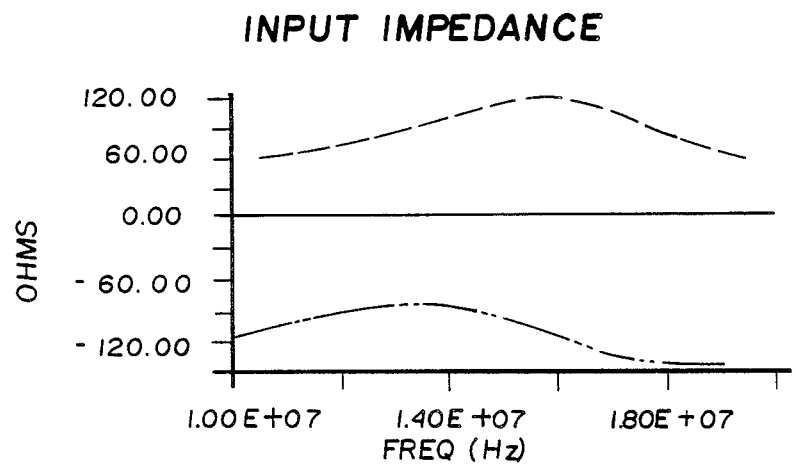
FIGS. 8A–8C are graphs of mathematically-calculated input impedances for the transducer shown in FIG. 7.

FIG. 8A shows the probe input impedance as a function of frequency. The parameter values from Table I were used to compute the impedance values shown.

Figure 8B:
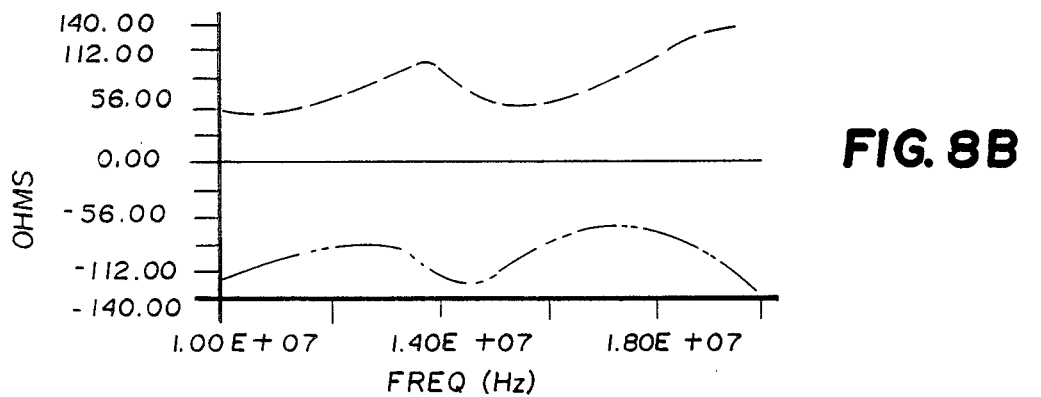
Figure 8C:
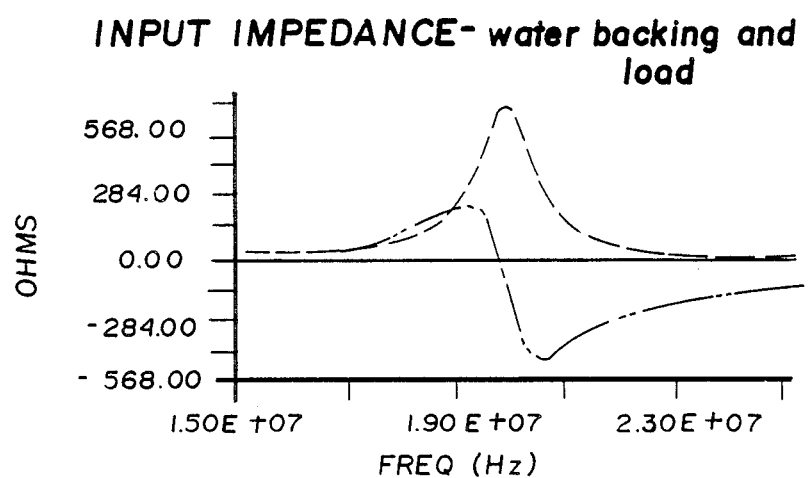

Table I shows the faceplate 128 thickness for $\frac{1}{4}$ wave matching. FIG. 8B shows the computed impedance for the faceplate; only the plate thickness was changed from the values shown in Table I. The differences between FIG. 8A and FIG. 8B may be important for some purposes. However, FIG. 8C shows the computed input impedance under the assumption that the ceramic transducer chip is simply loaded with water on each side. Comparison of the three figures (FIGS. 8A, 8B and 8C) shows that components can differ from the ideal and still provide major improvements over a "bare" water loaded ceramic.

FIG. 8A shows that total transducer impedance on the order of 75–100 ohms is attainable with PZT ceramic. The probe impedance has a considerable capacitive component which would ideally be "turned out" with an inductor if necessary. Because of space limitations, the usual inductive tuning at the ceramic is difficult; however, it is possible to place an inductive tuning circuit at the amplifier input (i.e., at switch 80 or connector 82) to "tune out" undesirable capacitive reactance resulting from piezoelectric element capacitance.

The impedance of microcable assembly 116, the input impedance of receiver 76, and the output impedance of pulser 74 should all be matched to the impedance of transducer 70 to obtain the most efficient energy transfer (microcables in the form of parallel wire transmission lines with a wire spacing to wire diameter ration of 10:1 are used in the preferred embodiment to provide 75 ohm impedance matching).

Although the ceramic thickness was chosen for a 20 MHz resonance, FIG. 8A indicates about 16 MHz center frequency. Ceramic loading from backing 128 and load cause this frequency shift (the shift is well known and expected).

Fabrication of the FIG. 6 catheter embodiment may require that the catheter body and transducer array 66 be assembled at the same time. In a preferred embodiment, transducer array 66 is fabricated separately as a subassembly 300 (as shown in FIGS. 9-13) so as to decrease the cost of fabrication, increase reliability, and permit the array to be fully tested before final assembly of catheter 52. Subassembly 300 is completely assembled and tested (and repaired if necessary) before it is incorporated into the catheter body, since it is difficult (or impossible) to repair transducer array 66 once it is disposed within catheter 52—and testing of the array at this late stage of fabrication typically only isolates completed catheters 52 that must be discarded.

Subassembly 300 includes: (a) a slotted octagonal sleeve infrastructure 302; (b) transducers 70; and (c) proximal lead insulation tubes 304. Slotted sleeve 302 (which takes on an octagonal shape when subassembly 300 is completely assembled) serves as a common backing/support structure for all of transducers 70 while providing structural integrity for the subassembly.

Figure 9:
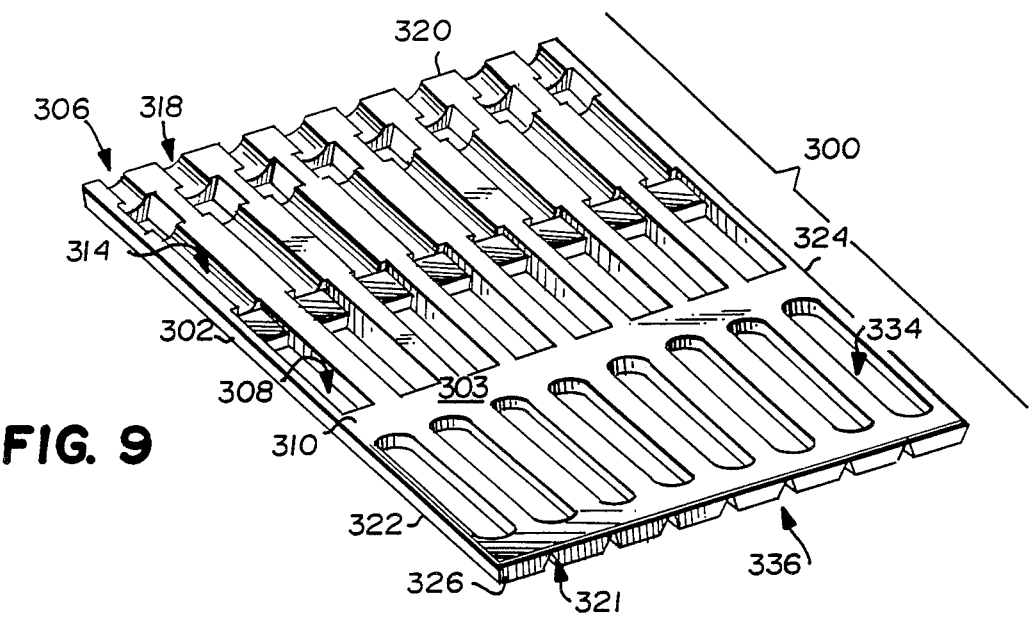
FIG. 9 is an elevated perspective view of an array subassembly infrastructure of the present invention prior to assembly of transducers thereto.
Figure 10:
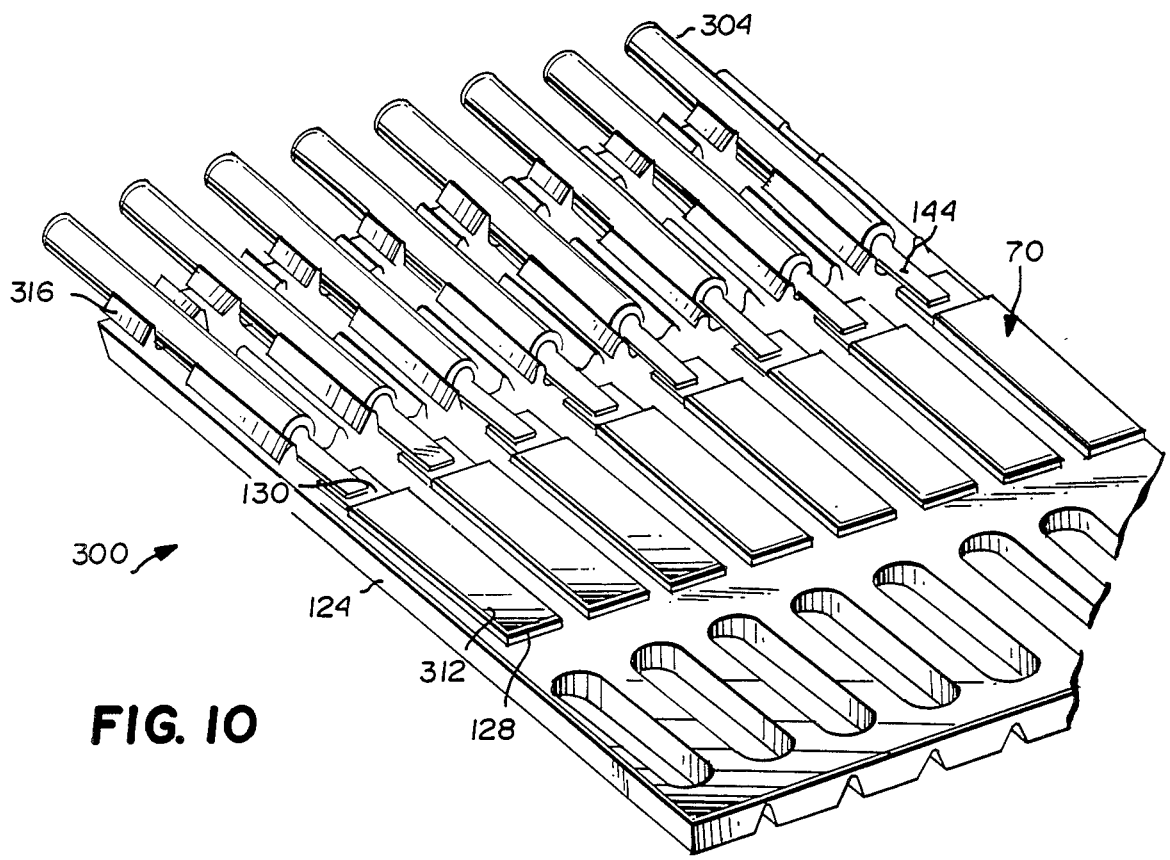
FIG. 10 is an elevated schematic view of the assembled array subassembly prior to curling into an octagonal shape.

Referring to FIG. 9, slotted sleeve 302 is a relatively flat sheet 303 of structural material (e.g., platinum, metal, plastic or other strong material) defining plural parallel slot-like depressions ("slots") 306 on an upper surface 310. The number of slots 306 equals the number of transducers 70 to be included in subassembly 300. Slots 306 are separated from one another on sheet lower surface 326 by fold gaps 321. Sheet 303 in the preferred embodiment has dimensions of about 0.015 inches by 0.015 inches.

Each slot 306 includes (or has associated with it): (a) means for mechanically retaining a transducer 70 of the type shown in FIG. 7; (b) means for guiding the lead(s) attached to the transducer to a point at which the leads attach to microcable assembly 116; and (c) means for retaining and insulating the transducer leads.

More particularly, slots 306 each include a rectangular cutout (aperture) 308. Cutouts 308 are each just large enough (e.g., 0.030 inches long) to accept and retain a transducer 70. A transducer 70 is mounted into each cutout 308 with the transducer backing 124 facing downward and faceplate 128 facing "upward" (when oriented as shown in FIG. 9). Cutouts 308 may (but need not necessarily) extend through the entire width of sheet 303.

As can perhaps best be seen in FIG. 12, transducers 70 are retained within cutouts 308 (which may have about 0.001 inch clearance on either side for transducer 70) by conductive epoxy 309. Cutouts 308 retain transducers 70 in place while providing no obstruction to acoustical energy radiating from and/or to faceplate 128. In the embodiment shown, faceplate 128 has dimensions which are larger (at least in the direction normal to the plane of FIG. 12) than the dimensions of transducer chip 126 so that the faceplate 128 "overlaps" cutout 308 and extends over sheet surface 310 in order to help retain the transducer in position while the mounting epoxy 309 cures.

Transducers 70 are mounted in cutouts 308 (preferably by a conventional automated micro-positioner assembly system which is used for accuracy and precision of assembly of parts with very small dimensions). Gold ribbon lead 130 is preferably already welded to the transducer chip surface 140. The leads 130 are the flattened ends of lead wires—and the insulated shanks of such lead wires are fitted within longitudinally-defined depressions 314 (FIG. 9) and clamps 316 to collectively serve as a strain relief for the transducer leads. The conductive (e.g., gold) ribbon 316 also improves electrical ground shielding of the individual lead wires.

After the transducers 70 and lead wires 304 have been assembled to flat sheet 303, the sheet is curled around catheter through-lumen 108 (a 0.025 inch diameter tube with a 0.002 inch wall thickness in this embodiment) to completely encircle the through-lumen. Longitudinal triangular-shaped gaps 321 (defined longitudinally along the entire length of sheet surface 326) open 45 degree wide "gaps" in surface 326 which provide longitudinal, axial fold lines 328 in the sheet. These fold lines prevent the sheet from breaking during the curling process by providing creases along which the sheet can be folded.

Sheet 303 is curled in the preferred embodiment so that gaps 321 close (i.e., the two sides of the triangular gaps contact one another). The sheet 303 side edges 322, 324 may be bonded together and to the catheter body (e.g., with epoxy) to prevent the sheet from uncurling. Once sheet 303 is closed in this manner, transducers 70 are disposed in relative positions as shown in FIGS. 5C-5D described earlier—and because sheet 303 folds along lines 328, the sheet outer surface 320 is octagonal in shape with planar portions separating each of the six fold lines (so that in cross-section the assembled subassembly 300 has the shape of a octagon)—each planar "side" portion carrying a transducer 70. The completed subassembly 300 is shown in FIG. 13.

After closing sheet 303 (and preferably also after testing fabricated subassembly 300 for electrical and mechanical characteristics and functionality), a length of tubing 340 (0.035 inches in diameter with a 0.005 inch thick wall in the preferred embodiment) is slid over lead wires 304 (preferably after cutting a slit in outer catheter wall) to allow all of leads to exit the subassembly 300 and be fed into the body of catheter 52—and also to allow the subassembly to be bonded to the catheter body. Apertures 334 defined through sheet 303 at the subassembly distal end 336 allow adhesive epoxy applied to the outer sleeve surface 326 to flow from the volume defined outside the subassembly 300 to the volume defined inside of the subassembly—so that a thin layer of polymer or other adhesive applied to the subassembly distal end bonds the subassembly to the through-lumen outer wall 122.

As can now be appreciated, it is extremely advantageous to integrate transducers 70 and microcable assembly 116 into a small, discrete subassembly 300. Array 66 and associated components can be manufactured and tested separately from catheter 52, and incorporated into the catheter only after full testing is completed.

In addition, subassemblies 300 with different transducer array configurations can be produced for different applications. For example, a longitudinal array of transducers 70 having substrate support, backing arrangements and electrical lead attachments consistent with minimum space requirements can be produced for longitudinal section imaging—and changes in catheter imaging capability can be made by fabricating catheters using a different (but structurally similar) subassembly structure.

Catheter 52 is shown in phantom in FIG. 13. Once subassembly 300 is assembled and tested, it is a relatively simple matter to incorporate it into catheter 52. The portion of through-lumen 108 which curled sheet 303 surrounds is cut or pulled away from the outer catheter tube 110 and the curved sheet is either wrapped around the through-lumen or slid over the lumen. After epoxing (through apertures 334) subassembly 300 to through-lumen outer wall 122 and positioning tubing 340, the catheter outer tube 110 is slid over the subassembly and the ends of conventional balloon 68 is bonded to the catheter outer tube. Subassembly 300 can be covered with a layer of insulation if necessary to prevent transducers 70 from electrically shorting (the face plates may, of course, also act as electrical insulators).

While array 66 carried by subassembly 300 includes four sets of diametrically opposed transducers 70 in the preferred embodiment, other configurations are also possible. A minimum of one transducer 70 is necessary for an ultrasound image to be produced. Additional transducers improve image resolution and allow a more complete image to be produced. Various non-symmetrical geometries of piezoelectric crystals may be used to provide unique beam patterns. Also, it may be desirable to position some transducers to provide a beam pattern which is axial to catheter tube 54 (or which is at some angle other than radial) in order to allow the physician to "look ahead" down the blood vessel and view an image of a section of the vessel which the catheter has not yet reached.

A curved quarter-wavelength faceplate geometry (as shown, e.g., in FIG. 5B) for transducer 70 might be used to provide a desired beam pattern—since in some applications (e.g., in catheters for very small blood vessels) it may be difficult to provide more than one or two transducers within the catheter due to lack of space—or additional imaging coverage may be required. Obtaining a strong ultrasonic reflection from an artery wall tends to require specific alignment of the outer surface of catheter 52 with the arterial wall. This requirement of strict alignment can be relaxed if the beam pattern of transducers 70 can be broadened somewhat by using a convex transducer or by positioning an ultrasonic lens over the piezoelectric element. Convex transducers can be grounded or molded ceramic material or film stretched over a properly shaped backing (e.g., a brass backing). An acoustic lens can be made of a material that "helps" acoustic impedance matching between the piezoelectric transducer chip and body tissue or blood. Convex transducers or acoustic lenses are most effective in the near field—the area of interest for catheter 52.

Another possible difficulty arises due to the requirement that at least a minimum distance should exist between transducer chip upper surface 140 and the closest target to be imaged (e.g., the vascular wall or a lesion or deposit adhering thereto). This requirement exists because the ultrasonic pulse transmitted by transducers 70 is much large in magnitude than the ultrasonic pulses received by the transducer (due to absorption of much of the energy in the transmitted pulse by body tissue). A return pulse cannot be readily detected by transducer 70 until the transmit pulse has decayed to a level below the receive pulse level.

For example, suppose ultrasonic transducer 70 has a relatively wide bandwidth and a Q (quality factor) of about 2 (that is, $f_0$/bandwidth=2). Assume transducer 70 resonates at about 20 MHz and has a bandwidth of approximately 10 MHz. Range resolution along the acoustic beam is inversely proportional to bandwidth and is given by the expression $$RR = c/2B,$$

where RR is range resolution, c is the speed of sound, and B is bandwidth. Thus, a wide-bandwidth transducer such as is shown in FIG. 7 has a range resolution of about 0.075 mm (for c=1500 m/s).

To first order accuracy, it is proper to assume that the initial transmit pulse produced by transducer 70 in response to electrical excitation dies away exponentially as $$x(r) = A_1 e^{-r/RR},$$

where r denotes range from the transducer.

The transmit pulse must decay to about $\frac{1}{2}A_2$ before a return pulse having amplitude $A_2$ can be detected by transducer 70. Solving for the necessary distance between transducer 70 and the target, $$A_1 e^{-r/RR} = A_2/2,$$
or
$$e^{-r/RR} = (1/2)(A_2/A_1).$$

Taking the natural log, $$-r/RR = \ln[(1/2)(A_2/A_1)]$$
or
$$r' = -RR \ln(A_2/(2A_1))$$

where r' is the needed separation between transducer 70 and the closest target to be imaged.

Pulser 74 typically generates an electrical pulse having an initial amplitude of about 100 volts. Receiver 76 typically amplifies the electrical signals produced by transducer 70 in response to the returning pulse by about 40 dB to generate a 1 volt output. 40 dB of amplification amounts to a gain of 100, and thus, the ratio of the amplitude of the return signal to the amplitude of the transmitted signal is about 1:10,000.

Substituting into the r' equation set forth above, $$r' = -0.075 \ln(1/20,000) = 0.075 * 9.9,$$

or $$r' = 0.74 \text{ mm}.$$

As can be seen, this calculated value for r' is rather large. However, actual experimental results indicate that acceptable imaging can be obtained with less than this minimum spacing between the closest target and transducer 70. Nevertheless, minimum spacing is a consideration which should be taken into account in the design of catheter 52.

To assure this minimum spacing exists, transducers 70 might be placed on the inner wall of catheter 52 so that the ultrasonic beam produced by each transducer passes across the catheter diameter and then into the artery (i.e., upper and lower chip surfaces 134, 140 are reversed from their obvious locations). This "transcatheter imaging" mode of operation requires special attention to the position of guidewire 88 with respect to array 66 (in order to prevent the guidewire from obstructing the ultrasonic beams produced by transducers 70), but allows image generation in smaller vessels than is possible with transducers mounted on the catheter wall and directing energy away from the catheter.

It may also be desirable to tune transducer array 66 to a range of different frequencies (e.g., 10 MHz–30 MHz or to excite the transducer in different ways to obtain more detailed information concerning tissue density and other properties (thus enabling the physician to better distinguish between and identify different tissues encountered).

Figure 14:
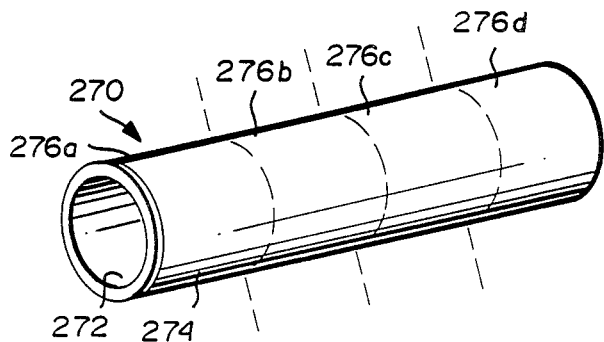
FIG. 14 is an elevated perspective view of an alternate transducer array subassembly of the present invention.
Figure 20:
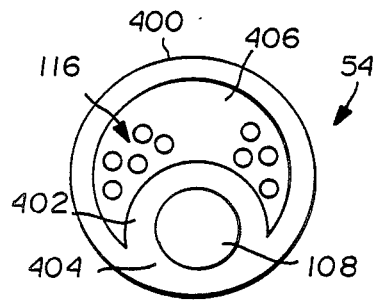
FIG. 20 is an elevated side view in cross-section of a still further embodiment of the present invention having an extruded, integral circular through-lumen and crescent ("smile") fluid lumen.

FIG. 14 shows a further embodiment of an ultrasonic transducer 270 having a tubular shape. Tubular transducer 270 can be fabricated by forming piezoelectric ceramic into a hollow tubular geometry, and further processing it into a tubular, high-density array of crystals. A conductive material 272 is applied to the inside of the tube to establish a common ground connection (metallic sputtering can be used to apply this material). The ceramic material must be polarized as part of preparation of transducer 270.

The outer transducer surface 274 can be subdivided into separate transducer elements using precision cuts while the inside surface 272 is kept intact to serve as a common ground connection. Small ribbon wires (not shown) are attached to the outer surfaces 276 for each element and connected to microcable assembly 116.

The curved transducer outer surface 274 has less angular sensitivity than the flat surface of the transducer shown in FIG. 7, and transducer 270 concentrates more discrete transducers within a smaller volume. In addition, a truly radial slice of artery can be imaged, mounting is simplified, and cost is reduced using the embodiment shown in FIG. 14.

Figure 15:
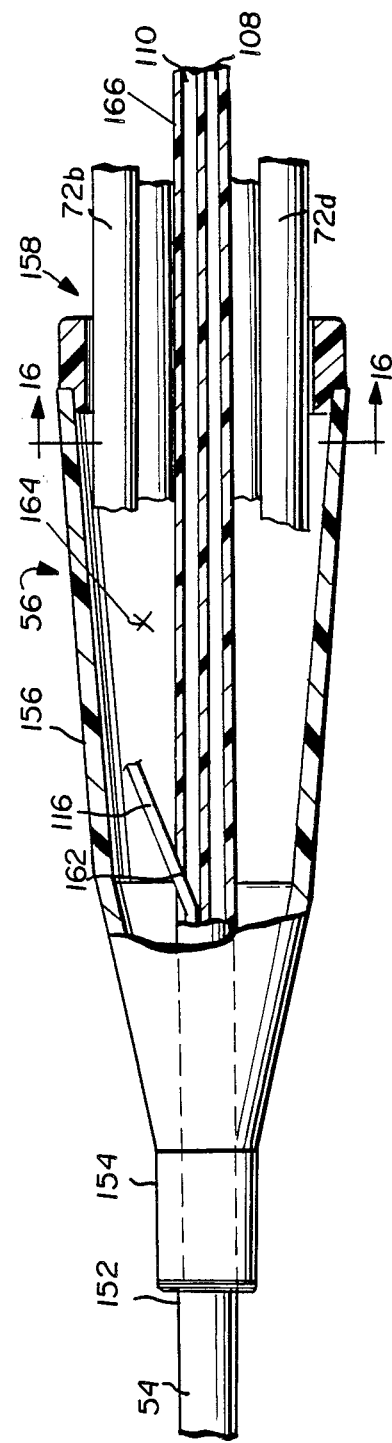
FIG. 15 is an elevated side view in partial cross-section of the proximal connector used to connect the catheter of FIG. 6 to the ultrasound excitation/imaging devices shown in FIG. 1.
Figure 17:
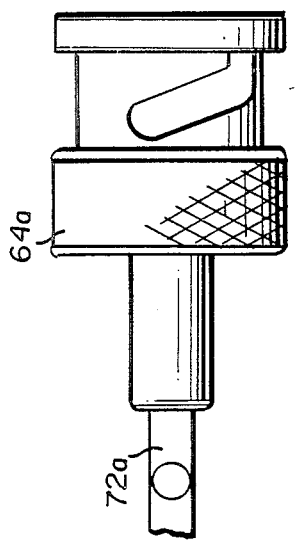
FIG. 17 is an elevated side view in perspective of a standard coaxial-type connector used in conjunction with the connector of FIG. 15.
Figure 18:
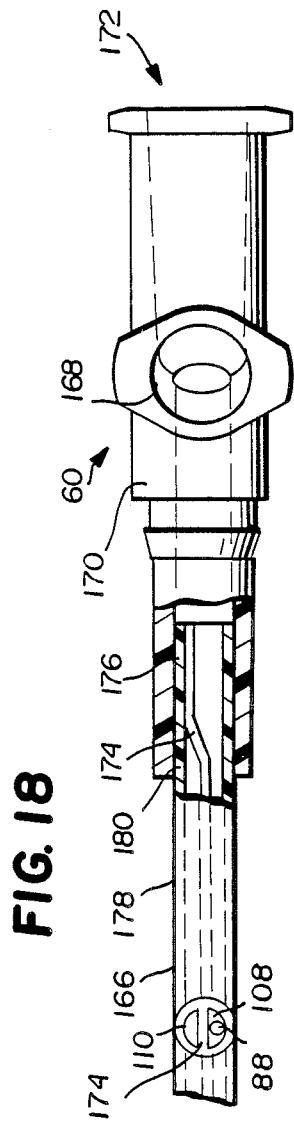
FIG. 18 is an elevated side view in partial cross-section of a standard mechanical connector used to connect the catheter tube of the present invention to the pump shown in FIG. 1.

FIG. 15 shows an exemplary proximal connector 56 used to connect the catheter tubing proximal end 152 to external devices (e.g., imaging device 62 and pump 58). Connector 56 includes a cable junction 154, a connector body 156, and a head 158 having circular apertures 160 drilled therethrough. Cable junction 154 is preferably hub-injection molded from urethane, and securely retains connector 56 to catheter tube 54. Microcable assembly 116 is lifted from within fluid lumen 110 at point 162 to make it available for connection to terminals 160. The leads of microcable assembly 116 are connected to coaxial cables 72 within connector body 156 at approximately point 164, these coaxial cables exiting the body of the connector via apertures 160 and each terminating in a conventional RF-type BNC coaxial connector 64 (see FIG. 17). Connector 56 is filled with urethane potting compound after assembly to prevent relative movement of the various cables and tubing it joins.

A catheter tubing 166 having only two lumen 108, 110 and no microcable assembly exits connector 56 and terminates in mechanical connector 60. Connector 60 connects catheter tubing section 166 to inflation pump 58 and/or to other standard, conventionl devices (e.g., blood pressure monitor, guidewire dispenser, or other commonly found medical diagnostic equipment or NDE equipment). A conventional side port leur 168 defined in connector body 170 is used for pressure monitoring and/or media infusion, while a proximal leur port 172 permits passage of guidewire 88. Catheter tube center web 174 (the layer of material separating lumen 108, 110) is reformed out of the way and bonded to connector hub 176. The catheter tube outside surface 178 is bonded to hub 176 using urethane adhesive 180.

Figure 19:
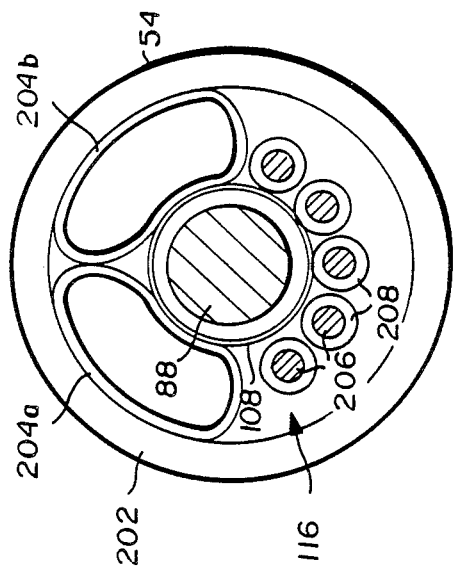
FIG. 19 is an elevated side view in cross-section of a further embodiment of the catheter tube of the present invention, this further embodiment having a coaxial lumen configuration.

FIG. 19 shows an alternative embodiment of catheter tubing 54 in accordance with the present invention. The embodiment shown in FIG. 19 has a coaxial lumen configuration—that is, guidewire lumen 108 is contained within and is located at substantially the center of a larger, outer polyethylene outside sheath 202. Inflation/deflation polyimid capillary tubes 204a 204b each having an effective inside diameter of 0.019 inches and a wall thickness of 0.0241 inches function as fluid lumen 110 to permit passage of saline solution to and from balloon 68 (two capillary tubes are used to ensure the effective cross-sectional diameter for fluid flow is sufficient to permit very rapid deflation of the balloon). Microcable bundle 116 in this embodiment includes 38 gauge copper conductors 206 each plated with silver and insulated with teflon coating 208.

FIGS. 20–23 show additional embodiments of catheter tube 54. In the FIG. 20 embodiment, catheter tube 54 includes a 0.060 inch diameter cylindrical outer tube 400 and a cylindrical inner tube 402 integral with the outer tube. The FIG. 20 tube is extruded as one piece, so that inner tube 402 shares an outer wall portion 404 in common with outer tube 400. The wall of outer tube 400 (including common wall portion 404) has a uniform thickness of 0.007 inch plus or minus 0.001 inch in the preferred embodiment.

Figure 6B:
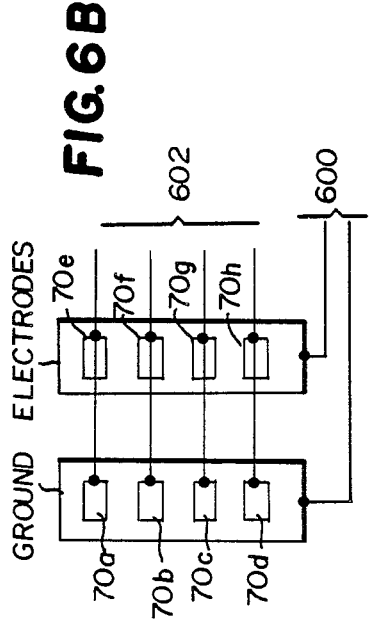
FIG. 6B is a schematic depiction of an eight transducer array using but 6 wire leads back to the signal generation and processing circuits.

Inner tube 402 defines a cylindrical passage having a diameter of 0.021 inch plus or minus 0.001 inch in the preferred embodiment which serves as thru lumen 108 (i.e., the inner tube contains guidewire 88). The crescent-shaped ("smile") volume 406 within outer tube 400 not occupied by inner tube 402 serves as fluid lumen 110 and also as a conduit for microcables 116 (9 microcables in the preferred embodiment for an 8 elements transducer array 66—one ground conductor and a conductor for each transducer). Alternatively, as depicted in FIG. 6B, only six lead wires need be used to accommodate eight transducers. This same crescent-shaped lumen 116 conducts contrast/saline solution for inflating balloon 68.

Figure 21:
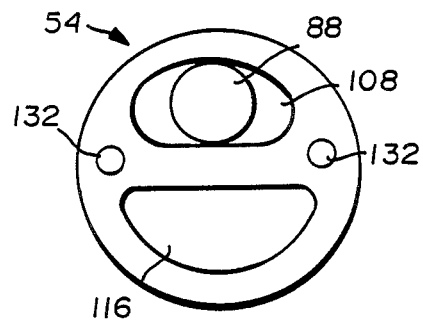
FIGS. 21–23 are elevated side views in cross-section of still further embodiments of catheter tubes of the present invention.
Figure 22:
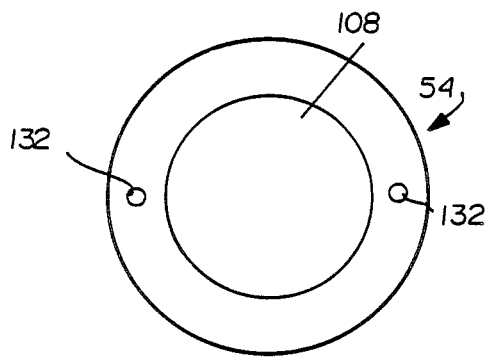

FIGS. 21 and 22 show catheter tubes in which some or all of microcables 132 are embedded within the polyethylene lumen wall. By embedding the microcables within the lumen wall, interior lumen space is not occupied by the microcables and thus, the diameter of the catheter tube can be significantly decreased. The preferred way of embedding the microcables within the lumen wall is to extrude the wall over the cables.

Figure 23:
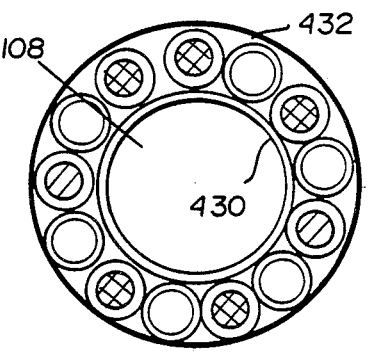
Figure 16:
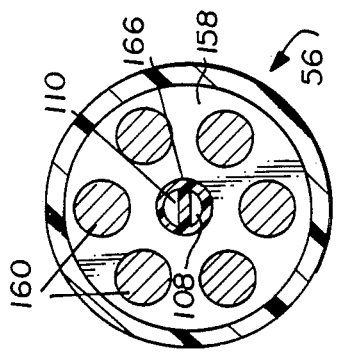
FIG. 16 is an elevated side view in cross-section of the proximal connector shown in FIG. 15.

In the FIG. 23 embodiment, coaxial inner and outer tubes 430, 432 are used in lieu of a single extruded tube structure. Inner tube 430 is an extruded polymer tube (e.g., polyethylene or teflon) having a diameter of about 0.056 mm—large enough to easily accommodate a 0.018 inch guidewire. Microcables (electrical cables and/or optical fibers) are helically wound around inner tube 430. Outer tube 432 is a shrink tube (i.e., made of a shrink film such as teflon) which is slid over the microcables and then heated to shrink it into conformance with the structures it encloses. This structure contains no fluid lumen so it cannot be used without modification for dilatation type catheters—but it is highly miniaturized and easy to assemble, and therefore finds utility in diagnostic-only catheter applications.

FIGS. 24–29 show some diagnostic-only catheters 500 which can be used in applications where dilatation is not needed. Catheters 500 have basically the same structures as the catheters described previously, except that they have no balloon for dilatation and do not require fluid lumens.

FIG. 24 shows a catheter 500 having a longitudinal transducer array 66 used to produce a longitudinal sectional image of a vascular segment of interest.

FIG. 25 shows a catheter 500 including three staggered pairs of transducers 70, while FIG. 26 shows a catheter having a single pair of opposing transducers.

FIG. 27 shows a catheter with a circular transducer array 66 used to produce a radial (cross-sectional) image at a particular vascular site.

FIG. 28 shows a catheter 500 with double staggered, circular radial transducer arrays 66 of transducers used to produce a radial (cross-sectional) image at a particular vascular site.

FIG. 29 shows a catheter 500 including a circular array of transducers 70 located near the distal end of the catheter (or recessed 0 to 2 centimeters from the catheter distal end) with an energized (faceplate) surface facing in a "look-ahead" position to produce an axial image in a vascular section. Individual transducer elements 70 may be angulated from 0 to 45 degrees from the vascular axis to produce different angle images. If transducers 70 are recessed from the catheter tip, polyethylene or similar material can be disposed at the tip to provide sufficient transmissivity of ultrasound energy for image generation.

Figure 30:
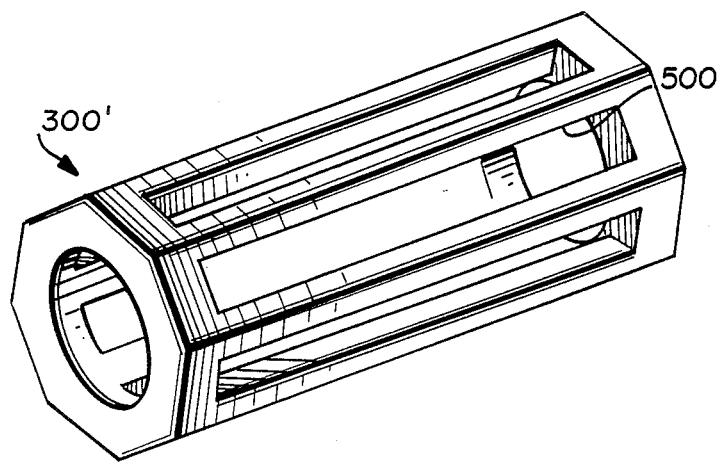
FIG. 30 is a perspective view of a solid stainless steel electro machined carriage into which eight transducers may be mounted prior to assembly on a catheter tube.
Figure 31:
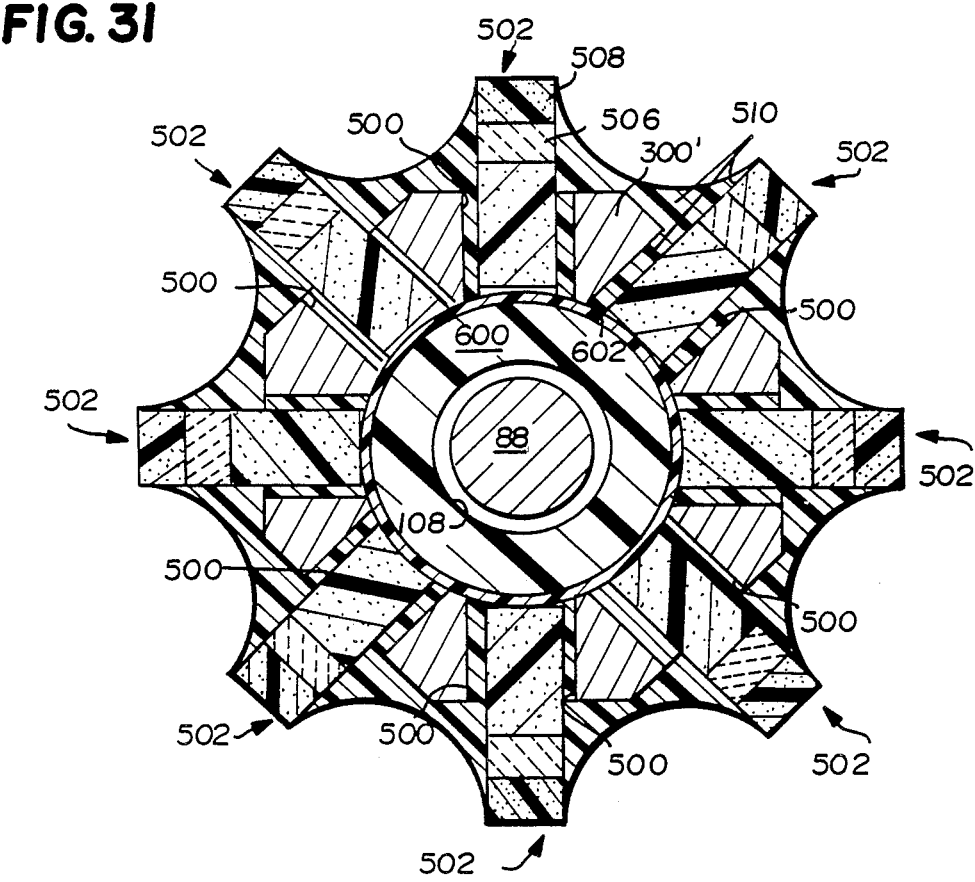
FIG. 31 is a cross-sectional view of an assembled transducer array subassembly (using the carriage of FIG. 30) mounted onto a catheter tube.

Instead of forming subassembly 300 by folding an initially flat carriage, a solid octagonal carriage 300' may be electromachined as shown in FIG. 30. Here each face of the cylindrical octagonal carriage has an aperture 500 into which an assembled ultrasonic transducer 502 can be epoxied—as shown in cross section at FIG. 31. Each transducer 502 includes the backing 504, active one-fourth wavelength piezoelectric layer 506 and impedance matching faceplate 508. Each transducer 502 is adhesively affixed within apertures 500 of carriage 300' by epoxy 510 to complete the transducer subassembly which is thereafter slid over catheter through-lumen walls 600 and epoxied thereto at 602. Guidewire 108 slidably passes through the center of catheter walls 600 with suitable clearance as depicted in FIG. 31.

A new balloon angioplasty catheter design having ultrasonic imaging capabilities has been described which is sufficiently miniaturized and reliable to be used in the manner that ordinary balloon-type catheters are presently used and yet provides real-time ultrasound images of arterial structure, character and response to intervention never before available in an angioplasty catheter. While the invention has been described in connection with what is presently considered to be its most practical and preferred embodiments, the invention is not limited to the disclosed embodiments but on the contrary, is intended to cover all modifications and alternate configurations included within the scope of the appended claims.

What is claimed is:

1. An ultra-thin electroacoustic transducer having an overall thickness less than 0.0075 inch and comprising:
   an active piezoelectric layer having a thickness of approximately one-fourth wavelength at its acoustic operating frequency and having an acoustic impedance $Z_1$;
   a backing layer affixed to a first face of said piezoelectric layer, said backing layer having an acoustic impedance $Z_2$ which is greater than $Z_1$;
   a faceplate layer affixed to a second, opposite, face of said piezoelectric layer, said faceplate layer having a thickness of approximately one-fourth wavelength at said operating frequency and having an acoustic impedance $Z_3$ which is approximately the geometric mean of $Z_1$ and an ambient acoustic impedance during use; and
   electrical lead means for making electrical connections to said first and second faces of the piezoelectric layer.

2. An ultra-thin electroacoustic transducer as in claim 1 wherein $Z_1$ is about $27 \times 10^6$ Kg/(M$^2$ sec) and $Z_2$ is about $30 \times 10^6$ to $40 \times 10^6$ Kg/(M$^2$ sec).

3. An ultra-thin electroacoustic transducer as in claim 1 wherein said electrical lead means includes metallic surfaces applied to said first and second faces of the piezoelectric layer and wherein said backing and faceplate layers each comprise an in situ cured layer of powders mixed with epoxy on respectively associated faces of the piezoelectric layer.

4. An ultra-thin electroacoustic transducer as in claim 1 wherein said backing and faceplate layers each comprise an in situ cured layer of an epoxy material respectively associated faces of the piezoelectric layer.

5. An ultra-thin electroacoustic transducer as in claim 1 wherein said backing layer comprises Tungsten powder mixed with epoxy.

6. An ultra-thin electroacoustic transducer as in claim 1 wherein said faceplate layer comprises $Al_2O_3$ powder mixed with epoxy.

7. An array subassembly of ultra-thin electroacoustic transducers comprising:
   a cylindrical carriage which includes means for defining (i) a plurality of circumferentially arranged wall apertures, and (ii) a through aperture along its axis; and
   a corresponding plurality of transducers adhesively mounted in respective said wall apertures and thereby disposed in a circumferentially extending array so as to provide an array subassembly of plural said transducers disposed within the wall apertures of said cylindrical carriage; and wherein at least one of said transducers has an overall thickness of less than 0.0075 inch and includes,
   (a) an active piezoelectric layer having a thickness of approximately one-fourth wavelength at its acoustic operating frequency and having an acoustic impedance Z1;
   (b) a backing layer affixed to a first face of said piezoelectric layer, said backing layer having an acoustic impedance Z2 which is greater than Z1;
   (c) a faceplate layer affixed to a second, opposite, face of said piezoelectric layer, said faceplate layer having a thickness of approximately one-fourth wavelength at said operating frequency and having an acoustic impedance Z3 which is approximately the geometric mean of Z1 and an ambient acoustic impedance during use; and
   (d) electrical lead means for making electrical connections to said first and second faces of the piezoelectric layer.

8. An array subassembly of ultra-thin electroacoustic transducers as in claim 7 further comprising a catheter tube adhesively affixed within said through aperture of the cylindrical carriage.

9. An array subassembly of ultra-thin electroacoustic transducers as in claim 8 wherein said catheter tube includes a through-lumen for slidably passing a guidewire therethrough.

10. An electroacoustic transducer array subassembly for mounting about a catheter sized to pass through human blood vessels, said subassembly comprising:
- a carriage structure having a generally cylindrical configuration and including means defining (i) a plurality of circumferentially spaced-apart wall apertures and (ii) an axially extending through aperture which is sized and configured to fit over at least a portion of said catheter; and
- plural electroacoustic transducers each of which includes a backing layer having a portion which extends into a respective said defined wall aperture and is affixed therewithin by means of a cured adhesive material, wherein
- said cylindrical carriage structure includes means which facilitate folding of an initially flat form of said carriage structure into said generally cylindrical configuration thereof, said fold-facilitating means including a number of axially extending regions of reduced material thickness which establish a corresponding number of axially extending fold lines, whereby said generally cylindrical configuration of said carriage structure is polygonal in cross-section.

11. An electroacoustic transducer array subassembly as in claim 10 wherein said cylindrical carriage is a solid body of material.

12. An electroacoustic transducer array subassembly as in claim 10 wherein said cylindrical carriage is made of a conductive metallic material.

13. An electroacoustic transducer array subassembly as in claim 10 wherein said cylindrical carriage includes wall apertures without transducers therein to facilitate subsequent adhesive affixation of the carriage to said catheter.

14. An electroacoustic transducer array subassembly as in claim 10 wherein said transducers include insulated lead wires connected therewith and said cylindrical carriage includes lead wire clamp means for relieving mechanical loads from connections to said transducers.

15. An electroacoustic transducer array subassembly for mounting about a catheter sized to pass through human blood vessels, said subassembly comprising:
- a carriage structure having a generally cylindrical configuration and including means defining (i) a plurality of circumferentially spaced-apart wall apertures and (ii) an axially extending through aperture which is sized and configured to fit over at least a portion of said catheter; and
- plural electroacoustic transducers each of which includes a backing layer having a portion which extends into a respective said defined wall aperture and is affixed therewithin by means of a cured adhesive material, wherein
- each said electroacoustic transducer is an ultra-thin transducer having an overall thickness less than 0.0075 inch and comprises:
  - (a) an active piezoelectric layer having a thickness of approximately one-forth wavelength at an intended acoustic operating frequency and having an acoustic impedance $Z_1$;
  - (b) a backing layer affixed to a first face of said piezoelectric layer, said backing layer having an acoustic impedance $Z_2$ which is greater than $Z_1$;
  - (c) a faceplate layer affixed to a second, opposite, face of said piezoelectric layer, said faceplate layer having a thickness of approximately one-fourth wavelength at said operating frequency and having an acoustic impedance $Z_3$ which is approximately the geometric mean of $Z_1$ and an ambient acoustic impedance during use; and
  - (d) electrical lead means for making electrical connections to said first and second faces of the piezoelectric layer.

16. An electroacoustic transducer array subassembly as in claim 15 wherein $Z_1$ is about $27 \times 10^6$ Kg/(M$^2$ sec) and $Z_2$ is about $30 \times 10^6$ to $40 \times 10^6$ Kg/(M$^2$ sec).

17. An electroacoustic transducer array subassembly as in claim 15 wherein said electrical lead means includes metallic surfaces applied to said first and second faces of the piezoelectric layer and wherein said backing and faceplate layers each comprise are in situ cured layer of powders mixed with epoxy on respectively associated faces of the piezoelectric layer.

18. An electroacoustic transducer array subassembly as in claim 15 wherein said backing and faceplate layers each comprise an in situ cured epoxy material on respectively associated faces of the piezoelectric layer.

19. An electroacoustic transducer array subassembly as in claim 15 wherein said backing layer comprises Tungsten powder mixed with epoxy.

20. An electroacoustic transducer array subassembly as in claim 15 wherein said faceplate layer comprises $Al_2O_3$ powder mixed with epoxy.

21. An electroacoustic transducer array subassembly as in claim 10 where said through aperture of said carriage is adhesively affixed to a catheter tube.

22. An electroacoustic transducer array subassembly as in claim 21 wherein said catheter tube has a through-lumen for slidably passing over a guidewire.

23. A dilatation angioplasty catheter of the type which is insertable into a blood vessel, said catheter comprising:
- a hollow, elongated tubular body of sufficiently small size so as to be insertable into a blood vessel and defining a central lumen therethrough and a fluid passageway;
- inflatable balloon means, fixedly disposed on an exterior portion of said body and fluid-connected to said fluid passageway, said balloon means varying in outside dimensions in response to fluid pressure with said fluid passageway; and
- ultrasonic transducer means dispoed within said central lumen of said body and surrounded by said balloon means, for producing acoustical signals and for sensing echoes of said produced signals, said transducer means including means (i) providing a substantially cylindrical array of individual ultrasonic transducers and (ii) defining a through aperture substantially coaxially disposed with respect to said central lumen.

24. An angioplasty imaging system including:
- a hollow, elongated tubular body defining a central lumen and a fluid passage therethrough, said body being of sufficiently small size and thereby adapted for insertion into a blood vessel;
- inflatable balloon means, fixedly disposed on an exterior portion of said body and fluid-connected to said fluid passage, said balloon means varying in outside dimensions in response to fluid pressure within said fluid passage;

ultrasonic transducer means disposed within said central lumen of said body and surrounded by said balloon means, said transducer means including a number of individual ultrasonic transducers arranged in a substantially cylindrical configuration so as to establish a through aperture in axial communication with said central lumen, each said ultrasonic transducers for producing acoustical signals in response to electrical excitation signals and for generating electrical signals responsive to echoes of said produced acoustical signals;

driver/imaging means for alternately (a) producing said excitation signals, and (b) generating an image of said blood vessel in response to said transducer means-generated electrical signals; and means disposed within said body for establishing a signal path between said drive/imaging means and said transducer means.

25. A system as in claim 24 wherein said driver/imaging means includes means for producing acoustic signals from said transducer means at a frequency of approximately 20 megahertz.

26. A miniature ultrasonic transducer small enough to be disposed within a vascular catheter body, said transducer comprising:

piezoelectric chip means for resonating at an operating frequency of approximately 20 MHz, said chip means having first and second opposing surfaces which establish therebetween a thickness of said chip means of approximately one-fourth wavelength at said operating frequency and having an acoustic impedance $Z1$;

backing means, disposed on said chip means first surface, and having an acoustic impedance $Z2$ which is greater than the acoustic impedance $Z1$ of said chip means for attenuating acoustical energy passing therethrough;

a layer of conductive material disposed on said chip means second surface and having a thickness of approximately one-fourth wavelength at said operating frequency and having an acoustic impedance $Z3$ which is approximately the geometric mean of $Z1$ and an ambient acoustic impedance during use;

a flattened electrical terminal electrically connected to said conductive material layer; and matching layer means, disposed on said conductive material layer and over said electrical terminal, said matching layer means defining a dimension which is an odd multiple of a quarter wavelength of said operating frequency, said matching layer means for increasing the efficiency of acoustical energy transfer to and from said chip means.

27. A miniature transducer array subassembly comprising:

cylindrical sleeve defining plural substantially planar outer surfaces;

a miniature ultrasonic transducer disposed on one of said plural outer surfaces, said transducer having at least one electrical connection;

lead wire means including a flattened electrically conductive distal end attached to said electrical connection of said transducer for electrically connecting said transducer; and means carried by said sleeve for affixation to said lead wire means for relieving stress from said connection, wherein said stree relieving means includes a longitudinal depression defined by means of said sleeve proximally of said one outer surface for receiving at least that portion of said lead wire means which is proximal to said flattened distal end thereof, and wire clamp means operatively associated with said defined depression for positionally retaining said proximal portion of said lead wire means within said defined depression.

28. A dilatation angioplasty cathether of the type which is insertable into a blood vessel, said catheter comprising:

a hollow, elongated tubular body defining a fluid passage therethrough;

inflatable balloon means, fixedly disposed on the exterior of said body and coupled to said fluid passage, said balloon means varying in outside dimensions in response to fluid pressure within said fluid passage;

piezoelectric chip means for resonating at an operating frequency of approximately 20 MHz, said chip means having first and second opposing surfaces which establish therebetween a thickness of said chip means of approximately one-fourth wavelength at said operating frequency and having an acoustic impedance $Z1$;

backing means, disposed on said chip means first surface, and having an acoustic impedance $Z2$ which is greater than the acoustic impedance $Z1$ of said chip means for attenuating acoustic energy passing therethrough;

a layer of conductive material disposed on said chip means second surface and having a thickness of approximately one-fourth wavelength at said operating frequency and having an acoustic impedance 23 which is approximately the geometric mean of $Z1$ and an ambient acoustic impedance during use;

a flattened electrical terminal electrically connected to said conductive material layer; and matching layer means, disposed on said conductive material layer and over said electrical terminal, said matching layer means defining a dimension which is an odd multiple of a quarter wavelength of said operating frequency, said matching layer means for increasing the efficiency of acoustical energy transfer to and from said chip means; and electrical cable means, disposed within said tubular body and electrically connected to said flattened electrical terminal, for conducting electrical signals to and from said terminal.

29. A dilatation angioplasty catheter of the type which is insertable into a blood vessel, said cathether comprising:

a hollow, elongated tubular body defining a fluid passage therethrough;

inflatable balloon means, fixedly disposed on the exterior of said body and coupled to said fluid passage, said balloon means varying in outside dimensions in response to fluid pressure within said fluid passage;

an electrically conductive cylindrical sleeve defining plural substantially planar outer surfaces, said sleeve enclosing at least a segment of said guide wire retaining passage;

a miniature ultrasonic transducer disposed on one of said sleeve plural outer surfaces, said transducer having first and second electrical connections;

lead wire means for electrically connecting to said transducer connections; and stress relieving means, carried by said sleeve for affixation to said lead wire means for relieving stress from said connections, said stress relieving means including a longitudinal depression for receifing at least a portion of said lead wire means, and clamp means operatively associated with said depression for positionally retaining said lead wire means within said depression.

30. A carriage structure for supporting a plurality of electroacoustic transducers, said carriage structure being foldable into a generally cylindrical configuration and thereby being adapted to surround an exterior portion of a catheter for electroacoustic imaging of human blood vessels and the like, said carriage structure comprising:

a substantially planar sheet member having upper and lower surfaces which define therebetween a thickness dimension;

means for defining a number of individual apertures in said sheet member which are sized and configured to accept a discrete electroacoustic transducer therein; and means for establishing a number of axially extending regions of said sheet member having a reduced thickness dimension as compared to the thickness dimension of said sheet member defined between said upper and lower surfaces thereof, to thereby define a number of fold lines which subdivide said planar sheet member into several planar regions having at least one of said apertures defined therein, wherein said established axially extending regions and said defined fold lines collectively provide means which facilitate folding of said carriage structure into said generally cylindrical configuration by allowing adjacent ones of said several planar regions to be angularly disposed relative to one another along a respective said fold line.

31. A carriage structure as in claim 30, wherein said means for establishing includes a number of axially extending grooves which are each defined in said lower surface.

32. A carriage structure as in claim 31, further comprising means for defining a number of second apertures for facilitating adhesive connection of said carriage structure to said catheter portion.

33. A carriage structure as in claim 32, wherein said second apertures are located at a distal end of said carriage structure as compared to said first-mentioned apertures.

* * * * *